(12) United States Patent
Toyama et al.

(10) Patent No.: US 9,990,735 B2
(45) Date of Patent: Jun. 5, 2018

(54) IMAGE GENERATION DEVICE THAT ACQUIRES IMAGES BASED ON A PERIODIC VARIATION OF AN ANATOMICAL STRUCTURE

(71) Applicant: KONICA MINOLTA, INC., Tokyo (JP)

(72) Inventors: Osamu Toyama, Kakogawa (JP); Hiroshi Yamato, Amagasaki (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days. days.

(21) Appl. No.: 14/390,697

(22) PCT Filed: Mar. 26, 2013

(86) PCT No.: PCT/JP2013/058662
§ 371 (c)(1),
(2) Date: Oct. 3, 2014

(87) PCT Pub. No.: WO2013/150911
PCT Pub. Date: Oct. 10, 2013

(65) Prior Publication Data
US 2015/0077432 A1    Mar. 19, 2015

(30) Foreign Application Priority Data

Apr. 4, 2012  (JP) ................. 2012-085581

(51) Int. Cl.
*G06T 7/254*        (2017.01)
*G06T 7/20*         (2017.01)
(Continued)

(52) U.S. Cl.
CPC ............ *G06T 7/2053* (2013.01); *A61B 6/486* (2013.01); *A61B 6/50* (2013.01); *A61B 6/5217* (2013.01);
(Continued)

(58) Field of Classification Search
None
See application file for complete search history.

(56) References Cited

U.S. PATENT DOCUMENTS

| 6,966,878 B2 | 11/2005 | Schoisswohl et al. |
| 2005/0049503 A1 | 3/2005 | Schoisswohl et al. |
(Continued)

FOREIGN PATENT DOCUMENTS

| CN | 201380018300.6 | 5/2012 |
| JP | 4-200457 A | 7/1992 |
(Continued)

OTHER PUBLICATIONS

International Search Report in International Application No. PCT/JP2013/058662, dated May 28, 2013, 2 pages.
(Continued)

*Primary Examiner* — Barry Drennan
*Assistant Examiner* — Diana Hickey
(74) *Attorney, Agent, or Firm* — Brinks Gilson & Lione

(57) ABSTRACT

An image generating apparatus includes: a diagnosis image generating section that generates, as a diagnosis image for every first time interval, at least one of a moving image in which a predetermined part of a human body or an animal is photographed and temporally continuous images based on the moving image; an image target setting section that acquires, for the diagnosis image, a first image at a predetermined time and a second image for every second time interval longer than the first time interval from the predetermined time; a pixel color converting portion that converts, of pixels of the first image and the second image, colors of pixels satisfying a predetermined condition to be distinguishable; and a display image generating section that generates an image for display using the first image and the
(Continued)

second image whose colors of the pixels have been converted by the pixel color converting portion.

23 Claims, 22 Drawing Sheets

(51) Int. Cl.
*A61B 6/00* (2006.01)
*G06T 7/00* (2017.01)
*G06T 11/00* (2006.01)
*G06T 5/50* (2006.01)

(52) U.S. Cl.
CPC ............ *G06T 5/50* (2013.01); *G06T 7/0012* (2013.01); *G06T 7/254* (2017.01); *G06T 11/001* (2013.01); *G06T 2207/10116* (2013.01); *G06T 2207/20224* (2013.01); *G06T 2207/30061* (2013.01)

(56) References Cited

U.S. PATENT DOCUMENTS

| | | | |
|---|---|---|---|
| 2006/0036172 A1* | 2/2006 | Abe | A61B 5/0048 600/443 |
| 2009/0105589 A1* | 4/2009 | Osaka | A61B 8/06 600/443 |
| 2010/0067660 A1* | 3/2010 | Maurer, Jr. | A61B 6/12 378/95 |
| 2010/0099991 A1* | 4/2010 | Snyder | A61B 8/483 600/454 |

FOREIGN PATENT DOCUMENTS

| | | |
|---|---|---|
| JP | 4404291 | 11/2004 |
| JP | 2005-074225 A | 3/2005 |
| JP | 3793102 | 4/2006 |
| JP | 2006-271484 A | 10/2006 |
| JP | 2007-289569 A | 11/2007 |
| JP | 2008-511368 A | 4/2008 |
| JP | 2010-268979 | 12/2010 |
| JP | 2012-061019 A | 3/2012 |
| JP | 2012-61019 A | 3/2012 |
| WO | WO 2006/025005 A2 | 3/2006 |

OTHER PUBLICATIONS

Aoki, Hirooki and Nakajima, Masato, "Unrestrained Respiration Monitoring for Sleeping Person Using Fiber Grating Vision Sensor," Dept. of E.E. Fac. of Sci. and Tec., Keio Univ., dated 2001, pp. 320-321, with English language translation.

Xu, Xin-Wei and Doi, Kunio, "Image feature analysis for computer-aided diagnosis: Accurate determination of ribcage boundary in chest radiographs," Med. Phys. 22 (5), dated May 1995, pp. 617-626.

Nakamori, Nobuyuki, et al., "Image feature analysis and computer-aided diagnosis in digital radiography: Automated analysis of sizes of heart and lung in chest images," Med. Phys. 17 (3), dated May/Jun. 1990, pp. 342-350.

Office Action dated May 5, 2016 regarding corresponding Chinese patent application 201380018300.6, twelve pages, including partial English-language translation of Office Action, 10 pages.

* cited by examiner

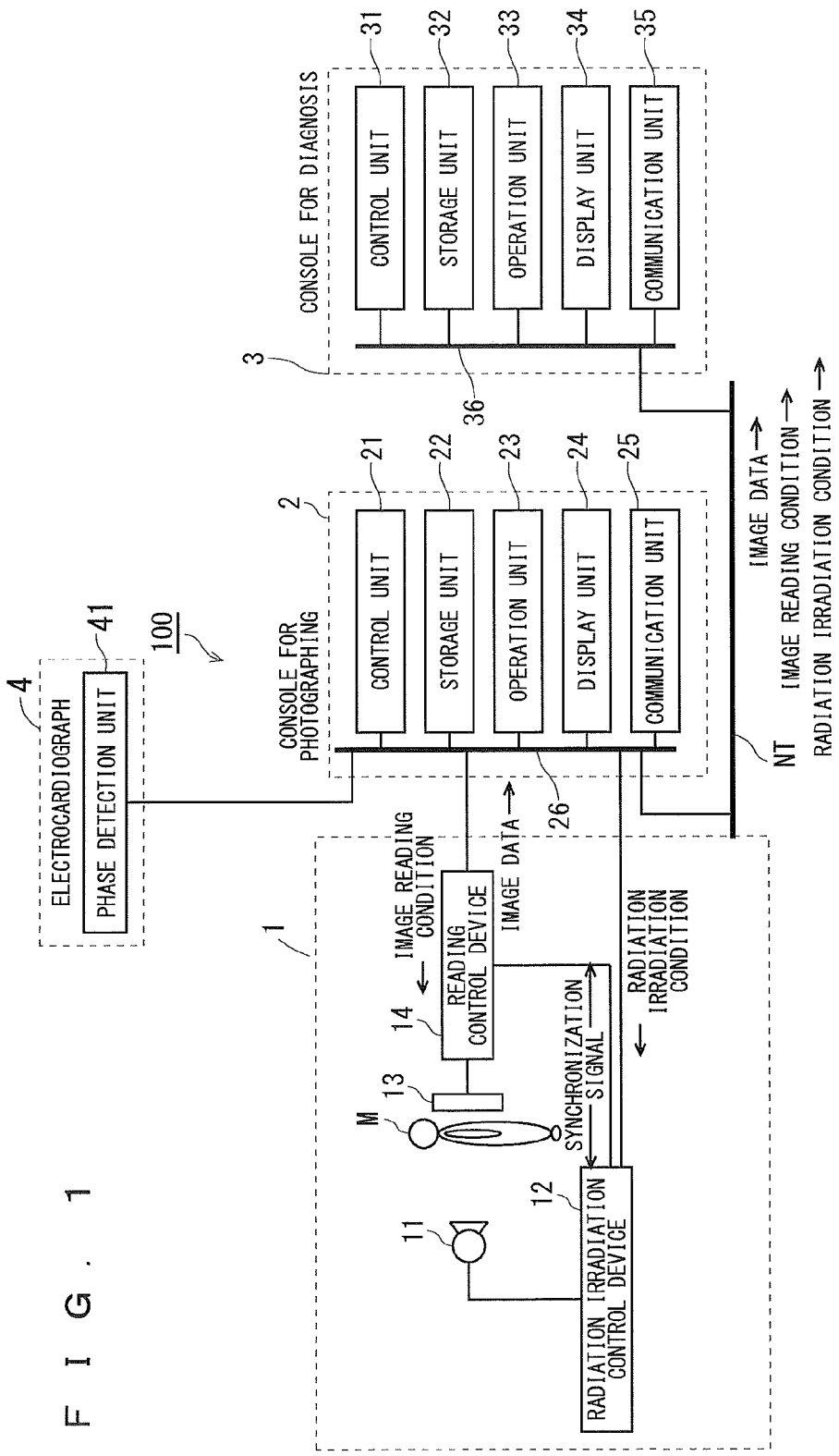

F I G. 2
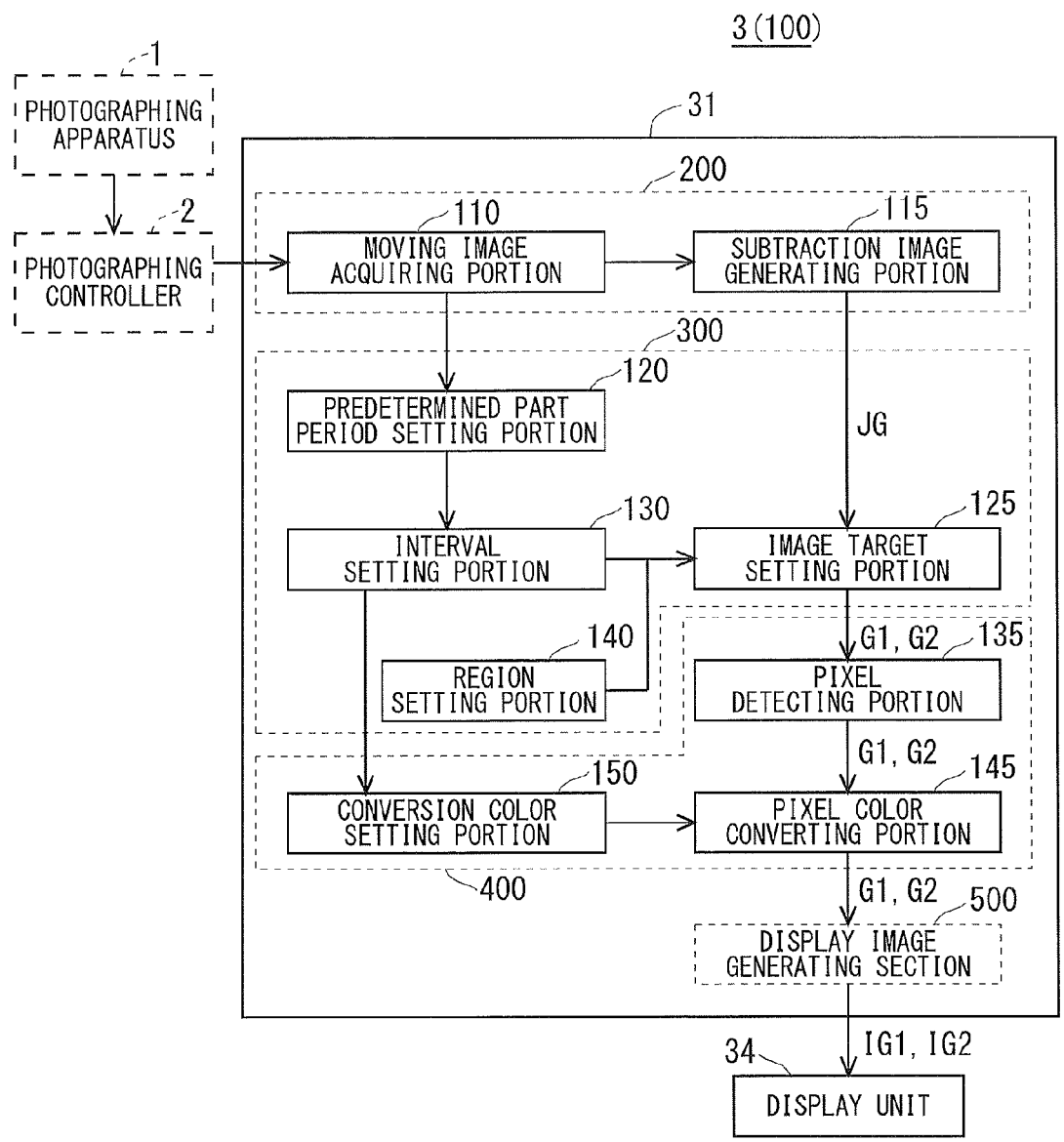

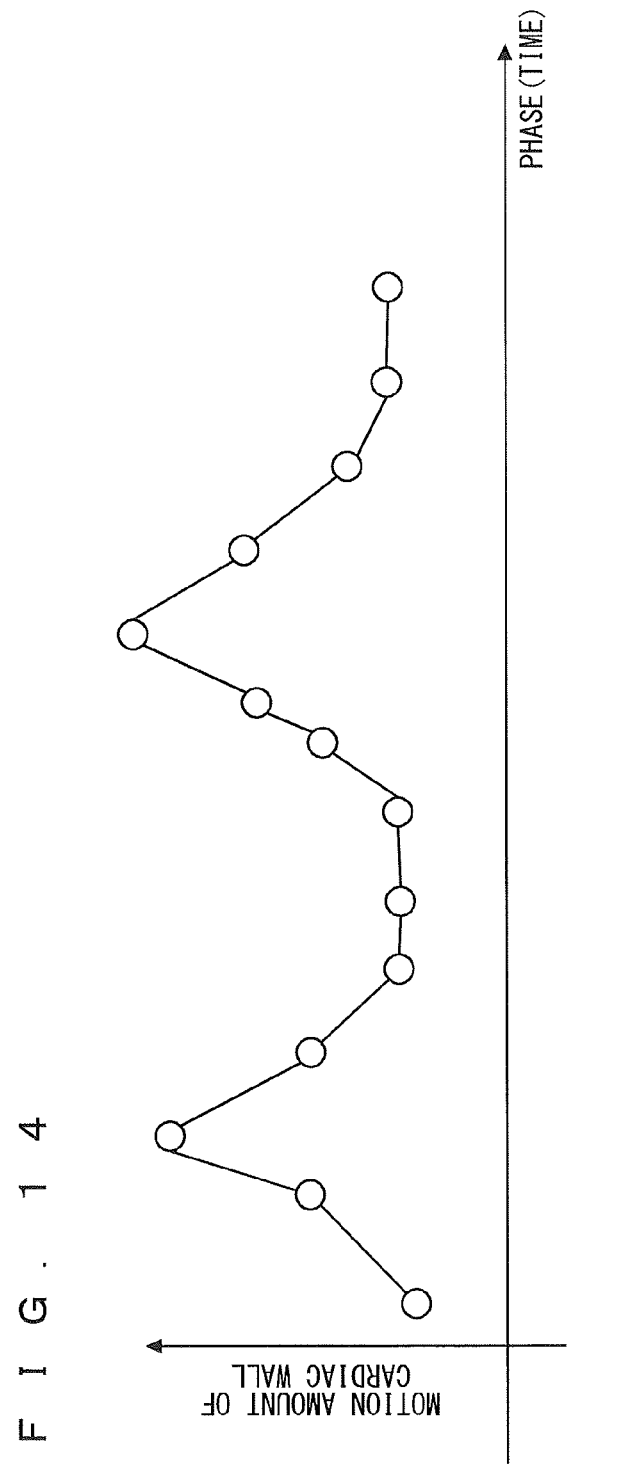

F I G . 1 5
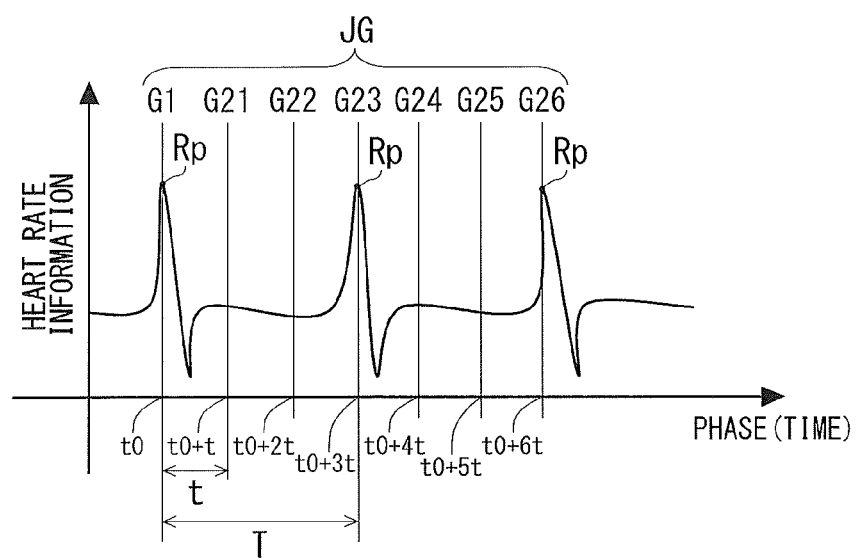

F I G. 1 6
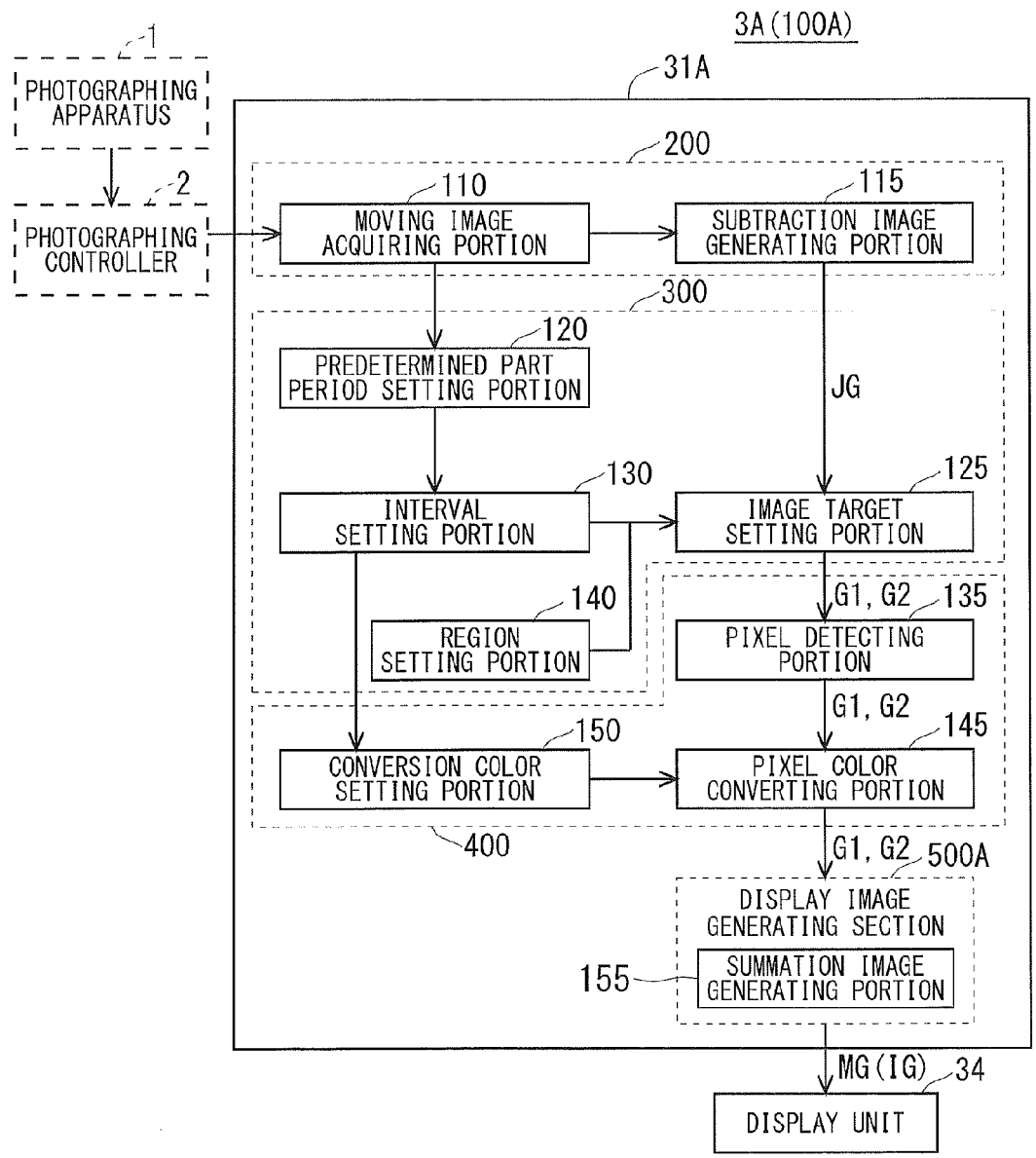

F I G. 1 7
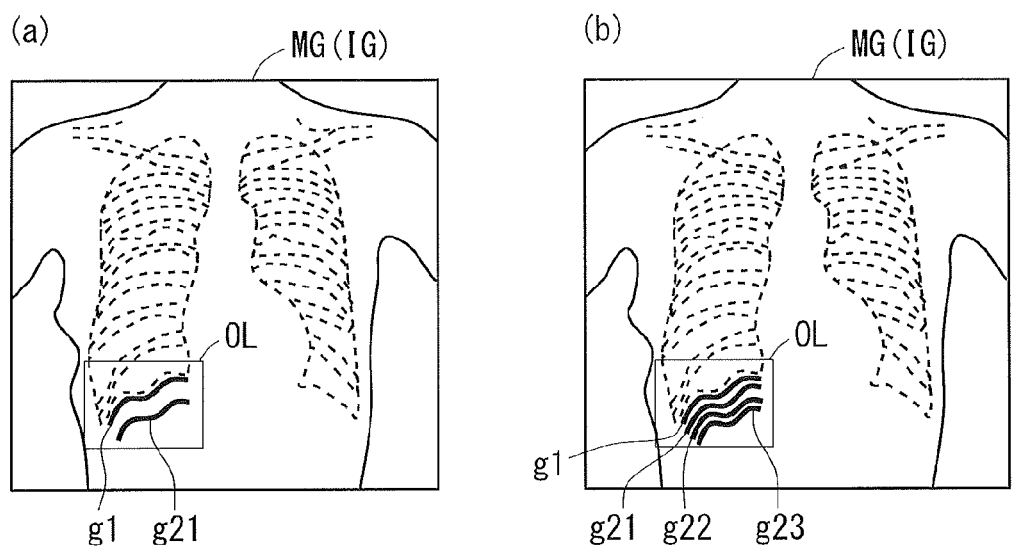
F I G. 1 8
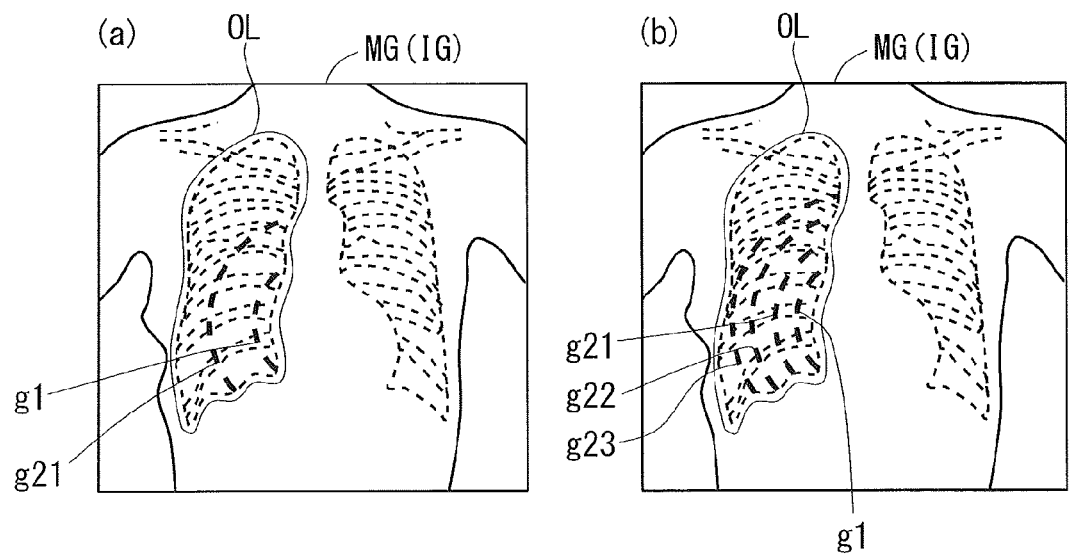

F I G. 1 9
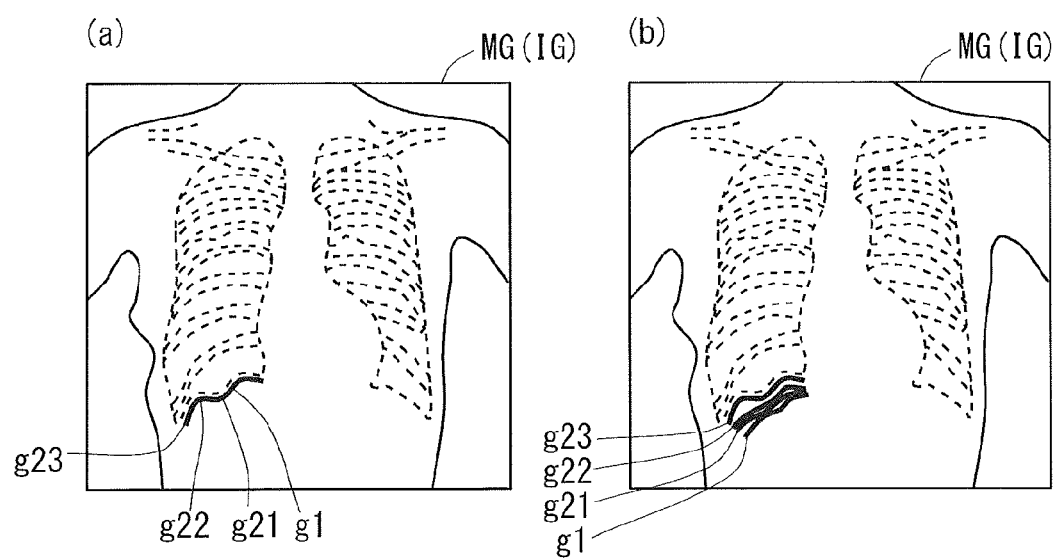

F I G . 2 1
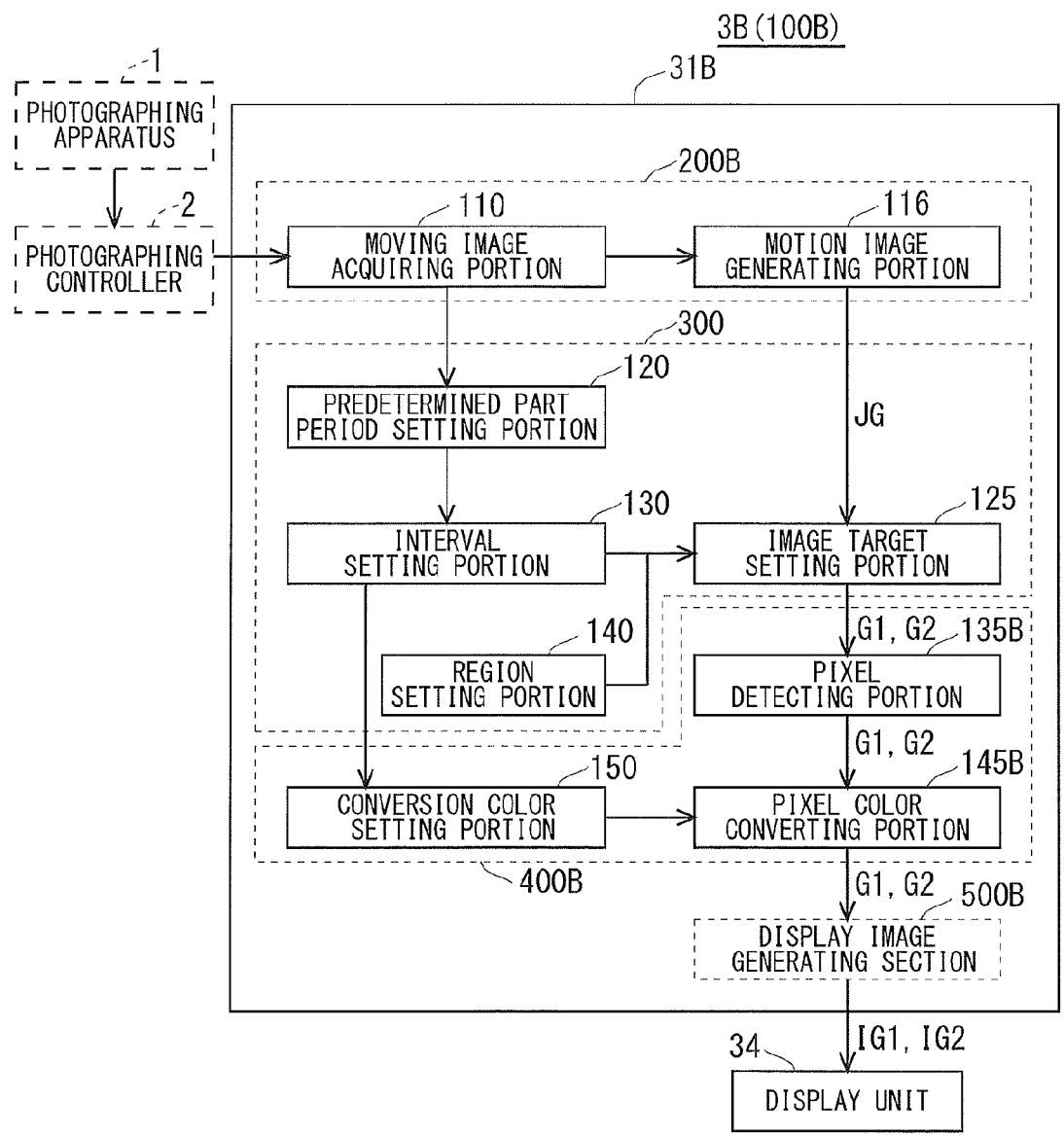

IMAGE GENERATION DEVICE THAT ACQUIRES IMAGES BASED ON A PERIODIC VARIATION OF AN ANATOMICAL STRUCTURE

This application is a National Stage application of International Application No. PCT/JP2013/058662, filed Mar. 26, 2013.

TECHNICAL FIELD

The present invention relates to a technology of generating a diagnosis image in which a predetermined part of a human body or an animal is photographed.

BACKGROUND ART

In the medical field, an affected area in the internal organs, skeletons, or the like is photographed with, for example, X-rays for various tests and diagnoses. Through the application of the recent digital techniques, a dynamic image in which the movement of an affected area is captured with X-rays or the like can be acquired relatively easily.

The recent digital techniques can photograph a dynamic image of a subject region including a target area using a semiconductor imaging sensor such as a flat panel detector (FPD), enabling the diagnosis by motion analysis of a target area, which could not have been made in still image photographing and diagnosis by conventional X-ray photography. For example, it is studied to extract the ventilation information in a lung field from a chest X-ray dynamic image and quantitatively analyze the dynamic function from the changes in the concentration and motion of the lung field, to thereby assist diagnosis/treatment (CAD for X-ray moving images).

For example, in the image forming technology disclosed in Patent Document 1, for a subtraction image based on a difference value between two successive images in a time axis direction, successive subtraction images are created in which gradations of the newest subtraction image and the time-elapsed subtraction image are gradually changed.

In the image processing technology disclosed in Patent Document 2, any one of the maximum value, minimum value, mean value, and median value of pixel values is taken as a pixel value to generate an image for each corresponding pixel group from a plurality of subtraction images.

In the moving image processing technology disclosed in Patent Document 3, time variations at the upper and lower positions of a diaphragm are calculated from the dynamic image of a chest, and a time variation of a pixel signal value in a small block of a lung field region is calculated, to thereby generate a display with a brightness value corresponding to a phase delay time of a time variation in a small block corresponding to the time variation of the diaphragm.

PRIOR ART DOCUMENTS

Patent Documents

Patent Document 1: Japanese Patent Application Laid-Open No. 2006-271484
Patent Document 2: Japanese Patent No. 4404291
Patent Document 3: Japanese Patent Application Laid-Open No. 2010-268979

SUMMARY OF THE INVENTION

Problem to be Solved by the Invention

The conventional technologies of Patent Documents 1 to 3 described above can visualize a temporally-varying motion through image analysis but suffer from a problem that change amounts at predetermined time intervals are difficult to be captured on images.

The present invention has been made in view of the above circumstances, and has an object to provide an image generating technology capable of accurately capturing, from a moving image in which a predetermined part of a human body or an animal is photographed, an amount of a state change of a predetermined part.

Means to Solve the Problem

An image generating apparatus according to an aspect of the present invention includes: a diagnosis image generating section that generates, as a diagnosis image for every first time interval, at least one of a moving image in which a predetermined part of a human body or an animal is photographed and temporally continuous images based on the moving image; an image target setting section that acquires, for the diagnosis image, a first image at a predetermined time and a second image after a second time interval longer than the first time interval from the predetermined time; a pixel color converting portion that converts, of pixels of the first image and the second image, colors of pixels satisfying a predetermined condition to be distinguishable; and a display image generating section that generates an image for display using the first image and the second image whose colors of the pixels have been converted by the pixel color converting portion.

An image generating apparatus according to another aspect of the present invention includes: a diagnosis image generating section that generates, as a diagnosis image for every first time interval, at least one of a moving image in which a predetermined part of a human body or an animal is photographed and temporally continuous images based on the moving image; an image target setting section that acquires, for the diagnosis image, a first image at a predetermined time and a plurality of second images respectively acquired at second time intervals longer than the first time interval from the first predetermined time; a pixel color converting portion that converts, among pixels of the first image and the second images, colors of pixels satisfying a predetermined condition to be distinguishable; and a display image generating section that generates an image for display using the first image and the second images whose colors of the pixels have been converted by the pixel color converting portion.

Effects of the Invention

The image generating apparatus of the present invention generates, as a diagnosis image for each of first time intervals, at least one of a moving image in which a predetermined part of a human body or an animal is photographed and temporally continuous images based on the moving image. The image generating apparatus acquires, for the diagnosis image, a first image at a predetermined time and second images respectively for second time intervals longer than the first time intervals. The image generating apparatus converts the colors of pixels satisfying a predetermined condition among the first image and second images, to thereby generate an image for display. As a result, an amount of a state change of the predetermined part can be visually recognized accurately from the first image and the second images. This improves the convenience of users and enables appropriate medical diagnosis.

BRIEF DESCRIPTION OF DRAWINGS

FIG. 1 shows an overall configuration of a radiation dynamic image photographing system according to embodiments.

FIG. 2 is a block diagram showing a functional configuration of an image generating apparatus according to a first embodiment.

FIG. 14 is a schematic view illustrating a variation cycle of a lateral width of a heart.

FIG. 15 is a schematic view showing waveform data of heart rate information in time sequence.

FIG. 16 is a block diagram showing the functional configuration of an image generating apparatus according to a second embodiment.

FIG. 17 is a schematic view illustrating the results generated by taking summation images as images for display.

FIG. 18 is a schematic view illustrating the results generated by taking summation images as images for display.

FIG. 19 is a schematic view illustrating the results generated by taking summation images as images for display.

FIG. 21 is a block diagram showing the functional configuration of an image generating apparatus according to a third embodiment.

DESCRIPTION OF EMBODIMENTS

1. First Embodiment

Figure 3:
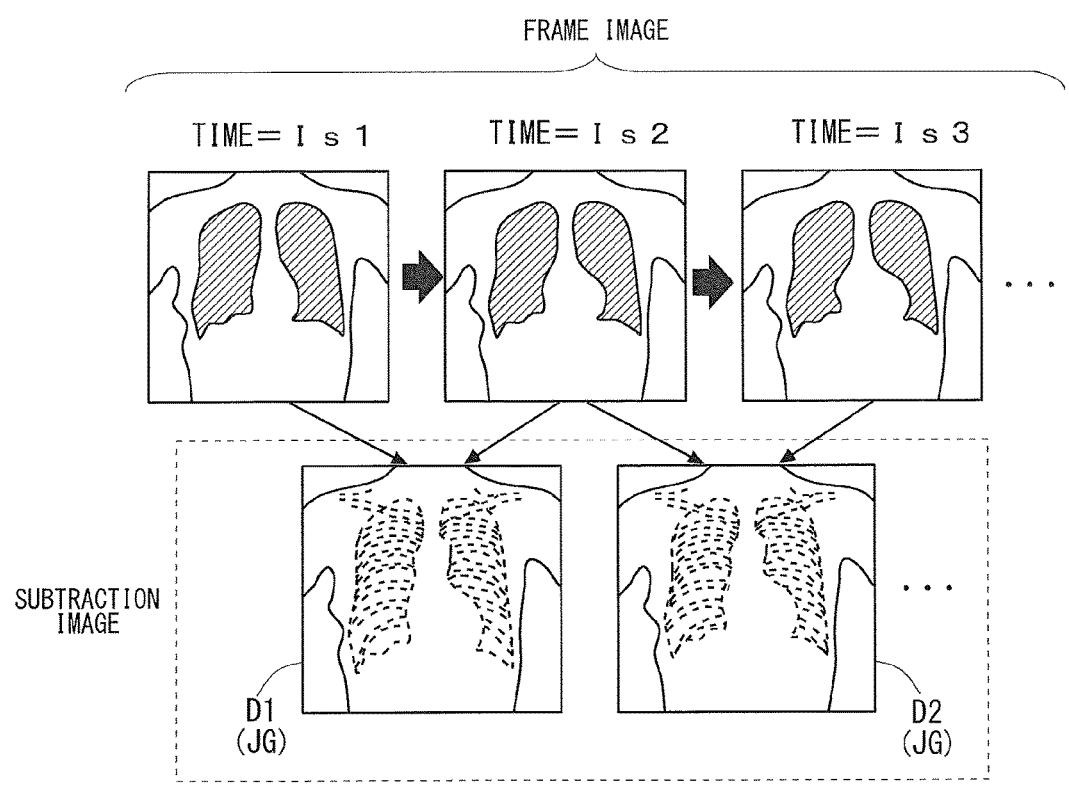
FIG. 3 is a schematic view describing the generation of subtraction images.

A radiation dynamic image photographing system according to a first embodiment of the present invention will be described below.

1-1. Overall Configuration of Radiation Dynamic Image Photographing System

The radiation dynamic image photographing system according to the first embodiment photographs a radiation image of a subject to generate a desired image for display, where the subject is a human body or an animal body. Particularly in this embodiment, an image according to the purpose of diagnosis is set and processed from the photographed radiation image, thereby improving diagnosis accuracy.

FIG. 1 shows the overall configuration of the radiation dynamic image photographing system according to the first embodiment. As shown in FIG. 1, a radiation dynamic image photographing system 100 includes a photographing apparatus 1, a photographing controller 2 (console for photographing), an image generating apparatus 3 (console for diagnosis), and an electrocardiograph 4. The photographing apparatus 1 and the electrocardiograph 4 are connected with the photographing controller 2 by means of a communication cable or the like, and the photographing controller 2 is connected with the image generating apparatus 3 through a communication network NT such as a local area network (LAN). The apparatuses constituting the radiation dynamic image photographing system 100 comply with the digital image and communications in medicine (DICOM) standard, and communications between the devices are performed in accordance with the DICOM standard.

<1-1-1. Configuration of Photographing Apparatus 1>

The photographing apparatus 1 is configured by, for example, X-ray equipment and photographs a dynamic state of the chest of a subject M involved in respiration. The dynamic state is photographed by repeatedly irradiating the chest of the subject M with radiation such as X-rays and, simultaneously, time-sequentially acquiring a plurality of images. A series of images obtained through such continuous photographing is referred to as a dynamic image (moving image). Each of the plurality of images constituting the dynamic image is referred to as a frame image.

As shown in FIG. 1, the photographing apparatus 1 includes an irradiation unit (radiation source) 11, a radiation irradiation control device 12, an image capturing unit (radiation detecting unit) 13, and a reading control device 14.

The irradiation unit 11 irradiates the subject M with the radiation (X-rays) under the control of the radiation irradiation control device 12. Illustrated as an example is a system for a human body, and the subject M corresponds to a test target. The subject M is also referred to as "test subject" below.

The radiation irradiation control device 12 is connected to the photographing controller 2 and controls the irradiation unit 11 based on the radiation irradiation condition input from the photographing controller 2 for radiography.

The image capturing unit 13 is configured by a semiconductor imaging sensor such as an FPD and converts the radiation, which has been radiated from the irradiation unit 11 and has passed through the test subject M, into an electrical signal (image information).

The reading control device 14 is connected to the photographing controller 2. The reading control device 14 controls switching portions of pixels of the image capturing unit 13 based on the image reading condition input from the photographing controller 2 to switch reading of the electrical signals stored in the pixels. Then, the reading control device 14 reads the electrical signals stored in the image capturing unit 13, to thereby acquire image data. After that, the reading control device 14 outputs the acquired image data (frame image) to the photographing controller 2. The image reading condition is, for example, a frame rate, a frame interval, a pixel size, and an image size (matrix size). The frame rate is the number of frame images acquired per second, which matches the pulse rate. The frame interval is a time between the start of the operation of acquiring one frame image and the start of the operation of acquiring the next frame image in continuous photographing, which matches the pulse rate.

Herein, the radiation irradiation control device 12 and the reading control device 14 are connected to each other and exchange synchronization signals with each other to synchronize the operation of irradiating radiation and the operation of reading images.

<1-1-2. Configuration of Photographing Controller 2>

The photographing controller 2 outputs the radio irradiation condition and the image reading condition to the photographing apparatus 1 to control the radiography and the operation of reading radiation images by the photographing apparatus 1 and, also displays the dynamic image, which has been acquired by the photographing apparatus 1, for checking whether or not it is an image suitable for a photographic engineer to check the positioning and make diagnosis.

As shown in FIG. 1, the photographing controller 2 includes a control unit 21, a storage unit 22, an operation unit 23, a display unit 24, and a communication unit 25. The respective units are connected to one another by means of a bus 26.

The control unit 21 is configured with a central processing unit (CPU), a random access memory (RAM), and the like. The CPU of the control unit 21 reads a system program and various processing programs stored in the storage unit 22 in response to the operation of the operation unit 23 and then develops them in the RAM. Then, the CPU of the control unit 21 executes various processes such as a photographing control process, described below, in accordance with the developed program, to thereby intensively control the operation of each unit of the photographing controller 2 and the operation of the photographing apparatus 1.

The storage unit 22 is configured by a nonvolatile semiconductor memory, a hard disk, and the like. The storage unit 22 stores various programs to be executed by the control unit 21 and the parameters required for executing the processes through the programs, or the data such the processing results.

The operation unit 23 includes a keyboard including cursor keys, numeric keys, and various function keys, and a pointing device such as a mouse, and outputs an instruction signal input through the key operation made on the keyboard, mouse operation, or a touch panel to the control unit 21.

The display unit 24 is configured with a monitor such as a color liquid crystal display (LCD), and displays an input instruction, data, or the like from the operation unit 23, in accordance with the instruction of the display signal input from the control unit 21.

The communication unit 25 includes a LAN adapter, a modem, a terminal adapter (TA), and the like, and controls the data transmission/reception with each device connected to the communication network NT.

<1-1-3. Configuration of Image Generating Apparatus 3>

The image generating apparatus 3 acquires a dynamic image transmitted from the photographing apparatus 1 through the photographing controller 2 and then displays an image for a doctor or the like to make diagnosis through reading.

As shown in FIG. 1, the image generating apparatus 3 includes a control unit 31, a storage unit 32, an operation unit 33, a display unit 34, and a communication unit 35. The respective units are connected to one another by means of a bus 36.

The control unit 31 is configured by a CPU, a RAM, and the like. The CPU of the control unit 31 reads the system program and various processing programs stored in the storage unit 32 in response to the operation of the operation unit 33 and then develops them in the RAM. Then, the CPU of the control unit 31 executes various processes in accordance with the developed program, to thereby intensively control the operation of each unit of the image generating apparatus 3 (details will be described below).

The storage unit 32 is configured with a nonvolatile semiconductor memory, a hard disk, and the like. The storage unit 32 stores various programs to be executed by the control unit 31 and the parameters required for executing the processes through the programs, or the data such the processing results. For example, the storage unit 32 stores the image generation processing program for executing an image generating process described below. The various programs are stored as the readable program codes, and the control unit 31 sequentially executes the operations according to the program codes.

The operation unit 33 includes a keyboard including cursor keys, numeric keys, and various function keys, and a pointing device such as a mouse, and outputs an instruction signal input through the key operation made on the keyboard, mouse operation, or a touch panel to the control unit 31.

The display unit 34 is configured with a monitor such as a color LCD, and displays an input instruction from the operation unit 33, the data, and an image for display described below, in accordance with the instruction of the display signal input from the control unit 31.

The communication unit 35 includes a LAN adapter, a modem, a TA, and the like, and controls the data transmission/reception with each device connected to the communication network NT.

<1-1-4. Configuration of Electrocardiograph 4>

Although FIG. 1 shows the electrocardiograph 4 apart from the test subject M, in actuality, each electrode terminal of the electrocardiograph 4 is attached to the test subject M to output an electrocardiographic waveform of the test subject M as a digital signal.

As shown in FIG. 1, the electrocardiograph 4 includes a phase detection unit 41. In response to a control signal from the CPU of the control unit 21, the phase detection unit 41 detects the phase of a heart rate of the subject M as the base information for synchronization of the imaging operation by the photographing apparatus 1.

Alternatively, the phase detection unit 41 can be provided in the photographing controller 2.

1-2. Specific Configuration of Image Generating Apparatus 3

The image generating apparatus 3 of the radiation dynamic image photographing system 100 in the first embodiment of the present invention generates an image from which an amount of the state change of the lung field can be visually checked, in association with a periodic time variation of the lung field (predetermined part) of the test subject M.

The functional configuration achieved in the image generating apparatus 3 will be described below.

<1-2-1. Functional Configuration of Image Generating Apparatus 3>

FIG. 2 shows the functional configuration achieved by the control unit 31, which is achieved through the operation of the CPU or the like in accordance with various programs, as well as other configuration in the image generating apparatus 3 of the radiation dynamic image photographing system 100. The image generating apparatus 3 in this embodiment uses a dynamic image in which the chest mainly including the heart and both lungs is photographed.

The control unit 31 is mainly composed of a diagnosis image generating section 200, an image target setting section 300, a pixel color converting section 400, and a display image generating section 500.

Although the following description will be given assuming that the functional configuration of the control unit 31 as shown in FIG. 2 is achieved through the execution of the pre-installed program, the functional configuration may be achieved with a dedicated hardware configuration.

The details of the processes performed by the diagnosis image generating section 200, the image target setting section 300, the pixel color converting section 400, and the display image generating section 500 will be described in order with reference to FIG. 2.

<1-2-1-1. Diagnosis Image Generating Unit 200>

The diagnosis image generating section 200 includes a moving image acquiring portion 110 that acquires a moving image and a subtraction image generating portion 115 that generates a subtraction image between frame images. The diagnosis image generating section 200 acquires a moving image, which captures the way in which a geometric state of a predetermined part of a human body or an animal changes with time, in time order by the moving image acquiring portion 110 and generates temporally continuous subtraction images (diagnosis images) based on the moving image by the subtraction image generating portion 115.

Details of the processes performed by the moving image acquiring portion 110 and the subtraction image generating portion 115 will be described in order with reference to FIG. 2.

<1-2-1-1-1. Moving Image Acquisition Portion 110>

The moving image acquiring portion 110 acquires a moving image capturing, in time order, the way in which a geometric state of a predetermined part of a human body or an animal changes with time, which has been photographed by the reading control device 14 of the photographing apparatus 1. Here, the predetermined part refers to a lung field region for the image generating apparatus 3 (see FIG. 2).

With reference to FIG. 2, the photographing controller 2 is located between the photographing apparatus 1 and the image generating apparatus 3, and the detection data stored in the storage unit 22 of the photographing controller 2 is output to the communication unit 35 of the image generating apparatus 3 through the communication unit 25.

<1-2-1-1-2. Subtraction Image Generating Portion 115>

The subtraction image generating portion 115 generates a subtraction image between ones of frame images of a moving image acquired in the moving image acquiring portion 110, that is, generates a moving image (subtraction moving image) from which a subtraction image can be reproduced in the form of video.

FIG. 3 is a schematic view describing the generation of subtraction images each between frame images for the frame images of a moving image acquired in the moving image acquiring portion 110. As shown in FIG. 3, for the frame images (still images) respectively photographed at times Is1 to Is3, a difference between the frame images is obtained with the time difference between the times Is1 and Is2 as a subtraction time difference, to thereby generate a subtraction image D1, and a difference between the frame images is obtained with the time difference between the times Is2 and Is3 as a subtraction time difference, to thereby generate a subtraction image D2. Here, the subtraction time difference in this embodiment is the frame interval per se of the moving image acquired by the moving image acquiring portion 110, which is approximately 0.067 second for a moving image of 15 frames per second (fps). The frame interval and subtraction time difference of the moving image can be set as appropriate time intervals, not limited thereto.

Differences between ones of images are obtained, and subtraction images DI (I is a finite integer) are arranged in time sequence, so that a subtraction moving image is generated. In this embodiment, the time interval (first time interval) of the subtraction images DI matches the frame interval of the moving image acquired by the moving image acquiring portion 110, which is approximately 0.067 second similarly to the subtraction time difference. The time interval of the subtraction images DI is not limited to the above-mentioned interval but may be set as an appropriate time interval, which is a relatively short time interval suitable for display in the form of video. The generated subtraction images DI are stored in the storage unit 32 as a diagnosis image JG.

<1-2-1-2. Image Target Setting Unit 300>

The image target setting section 300 includes a predetermined part period setting portion 120, an image target setting portion 125, an interval setting portion 130, and a region setting portion 140. The image target setting section 300 acquires, for the diagnosis image JG, a first image at a predetermined time and m (m is a positive integer) newest second images that are respectively obtained at image acquisition intervals (second time intervals) starting from the predetermined time (the predetermined time is not included in the image acquisition intervals). The image acquisition intervals (second time intervals) in this case are set to the time intervals suitable for diagnosis, which are longer than the time interval (first time interval) of the subtraction image DI described above.

Hereinafter, the details of the processes performed by the predetermined part period setting portion 120, the image target setting portion 125, the interval setting portion 130, and the region setting portion 140 will be described in order with reference to FIG. 2.

<1-2-1-2-1. Predetermined Part Period Setting Portion 120>

The predetermined part period setting portion 120 sets a predetermined part period being a periodic variation of the predetermined part. Then, the image target setting section 300 sets the second time intervals based on the predetermined part period.

To be specific, the predetermined part period setting portion 120 of this embodiment detects periodic time variations of the lungs of the test subject M, that is, detects the phase information and frequency (period) information on respiration. Herein, the detection of time variations refers to the detection of time variations of the geometric state such as the contour of the organ.

Description will be given below of the method of calculating the period information on respiration.

In this embodiment, as shown in FIG. 2, the predetermined part period setting portion 120 calculates an area value or a distance between the feature points of the lung field portion using the photographed image acquired by the moving image acquiring portion 110, to thereby acquire respiratory information. In other words, the moving image acquiring portion 110 in the diagnosis image generating section 200 can output a moving image to the predetermined part period setting portion 120 (see FIG. 2), and the predetermined part period setting portion 120 detects a respiratory cycle based on the area value or the distance between the feature points (the shape of a predetermined part) of the lung field region captured in the moving image. The way of obtaining the area of the lung field portion involves extracting the contour of the lung field portion and defining the number of pixels in the region surrounded by the contour as the lung field region.

Figure 4:
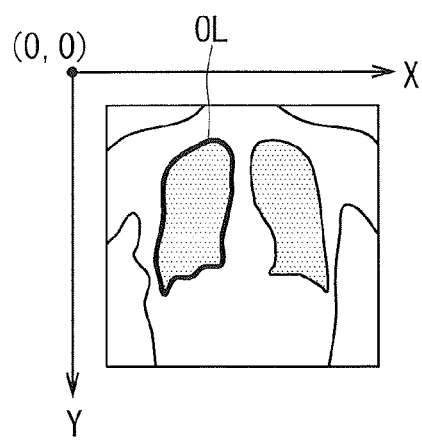
FIG. 4 is a schematic view illustrating a contour extraction of a lung field region.

FIG. 4 is a schematic view illustrating the contour extraction of the lung field portion. The lung field portion may be extracted for each of the left and the right as shown in FIG. 4 or may be extracted as the contour including the regions of the heart and the spine. The conventional technology is adoptable as the extraction method (see, for example, "Image feature analysis and computer-aided diagnosis: Accurate determination of ribcage boundary in chest radiographs", Xin-Wei Xu and Kunio Doi, Medical Physics, Volume 22(5), May 1995, pp. 617-626).

As described above, the predetermined part period setting portion 120 extracts a contour OL of the lung field portion using the photographed image acquired, and then takes the number of pixels in the extracted region as a feature amount to detect the feature amount as the area of the lung field region.

The distance between the feature points of the lung field region may be calculated as the respiratory information using the photographed image acquired by the moving image acquiring portion 110. In other words, the lung field portion is extracted as in the manner described above, the two feature points are obtained from the extracted region, and the distance between the two points is obtained, to thereby calculate a feature amount.

Figure 5:
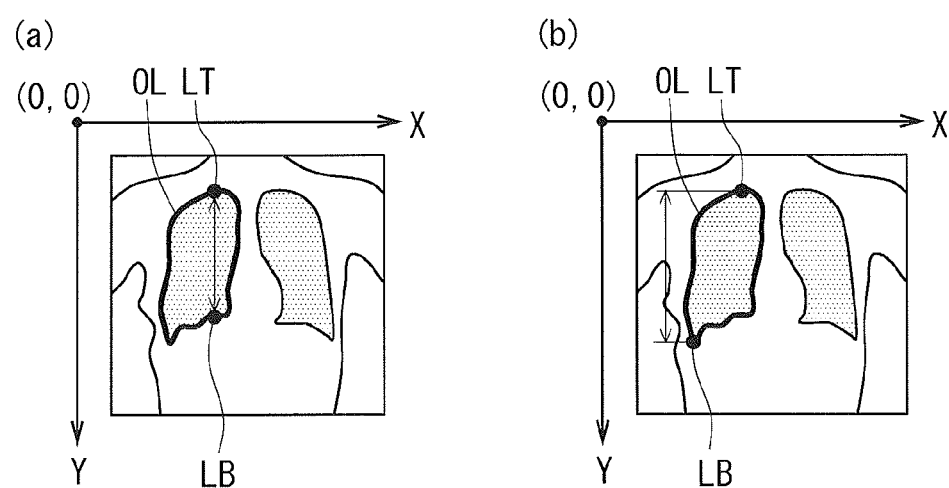
FIG. 5 is a schematic view illustrating positions of feature points in the lung field region.

FIG. 5 illustrates the positions of the feature points of the lung field region. In the case where a change in the length (lung field length) between an upper end LT to a lower end LB of the long region is calculated, part (a) of FIG. 5 shows an example in which extraction is performed assuming that the apical portion of the lung is the upper end LT and an intersection between the straight line drawn from the apical portion of the lung in the body axis direction and the diaphragm is the lower end LB of the lung region, and part (b) of FIG. 5 shows an example in which extraction is performed assuming that the apical portion of the lung is the upper end LT of the lung region and the costophrenic angle is the lower end LB of the lung region.

The predetermined part period setting portion 120 extracts the contour OL of the lung field region using the photographed image acquired, obtains the distance between the feature points from the extracted region, and detects the distance between the feature points, to thereby set a respiratory cycle.

As described above, the predetermined part period setting portion 120 detects a respiratory cycle based on a temporal change (a change in the shape of the predetermined part) of the area value or the distance between the feature points of the lung field region, which has been captured in a moving image. Therefore, a respiratory cycle can be acquired automatically based on a temporal change (a change in the shape of the predetermined period) of the area value or the distance between feature points of the lung field region, which has been captured in a moving image.

To remove noise components, in the respiratory information detection method in this image processing, the predetermined part period setting portion 120 preferably detects a respiratory cycle using frequency analysis based on a temporal change (a change in the shape of the predetermined part) of the area value or the distance between feature points of the lung field region. In other words, frequency analysis is performed on the fluctuations (sec FIG. 6) in the time-axis direction of the partial image (region of the contour OL of the lung field portion in FIGS. 4 and 5) capturing the area value or the distance between feature points of the lung field region. As a result, desired fluctuation components excluding the noise components can be extracted automatically, to thereby more accurately grasp a temporal change (an amount of the state change of a predetermined part) of the area value or the distance between feature points of the lung field region.

Although the respiratory information is obtained using a photographed image in this embodiment, the measurement result obtained by the external device may be used. In this case, the external equipment inputs the information about a respiratory cycle to the predetermined part period setting portion 120. In the measurement method by an external device, for example, the device described in Japanese Patent No. 3793102 can be used. Alternatively, for example, the monitoring technique using the laser light and the sensor composed of a CCD camera is adoptable (see, for example, "A Study on respiration monitoring of a sleeping person with FG vision sensor", Hirooki Aoki, Masato Nakajima, The Institute of Electronics, Information and Communication Engineers, Society Conference, Proceedings 2001, Information, System Society Conference Report, pp. 320 and 321, 2001 Aug. 29). In other words, respiratory information can be obtained also by the method in which the movement of the chest of the subject M is detected, for example, through laser radiation or with a respiration monitoring belt, or the method in which an airflow of respiration is detected with an airflow meter. Those methods are also applicable.

<1-2-1-2-2. Interval Setting Portion 130>

The interval setting portion 130 sets a period split time t, winch is one k-th (k is a positive integer) of a predetermined part period T set in the predetermined part period setting portion 120, and the number m of second images satisfying m≥k. For example, a user may interactively set k and m with a slider bar or the like while viewing an image or may input the values of k and m to the image generating apparatus 3 in advance.

Figure 6:
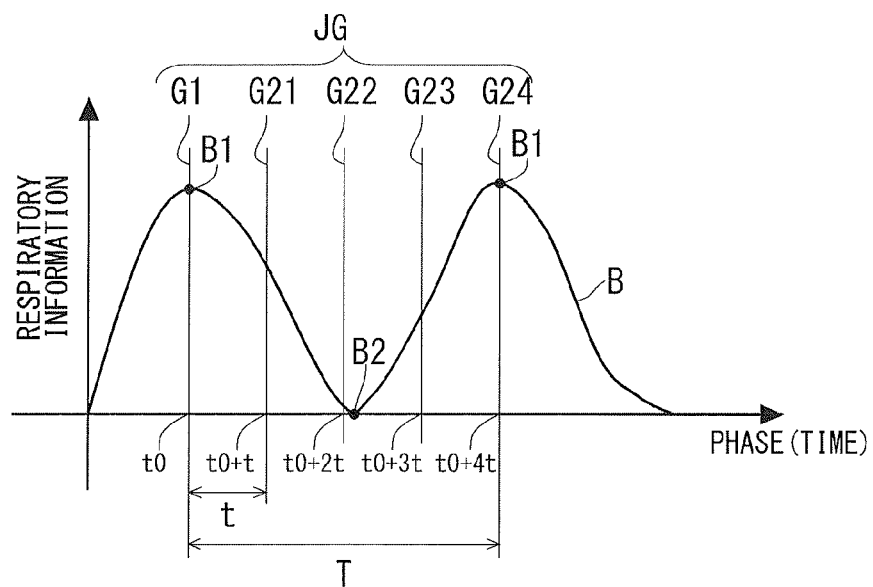
FIG. 6 is a schematic view showing wave data of respiratory information in time sequence.

FIG. 6 is a schematic view showing waveform data of the respiratory information detected in the predetermined part period setting portion 120 in time sequence. The vertical axis of FIG. 6 corresponds to a temporal change in the area value or the distance between feature points of the lung field region. That is, FIG. 6 shows the results obtained by adopting the respiratory information detection method described above to calculate a feature amount and perform monitoring in the time direction.

As shown in FIG. 6, one period of a cycle of respiration (respiratory cycle) B is composed of inhalation and expiration, one exhalation and one inhalation. In inhalation, the region of the lung field in the rib cage becomes larger as the diaphragm descends for inhaling. The time of inhaling to the extent possible (a point of time at which inhalation is changed to expiration) is a maximum inhalation time B1. In exhalation, the region of the lung field becomes smaller as the diaphragm ascends for exhaling. The time of exhaling to the extent possible (a point of time at which exhalation is changed to inhalation) is a maximum exhalation time B2. With reference to FIG. 6, the predetermined part period setting portion 120 sets the respiratory period T based on the maximum inhalation time B1, and then, the interval setting portion 130 sets the cycle split time t of the cycle T. Described here is an example in which k=4 is adopted and the period split time t, being one fourth of the period T, and m=4 are set. For example, the period split time t is one second if the respiratory period T is four seconds.

As described above, the predetermined part period setting portion 120 and the interval setting portion 130 set the image acquisition intervals to determine the times of the first image G1 and m second images G2 among the moving images acquired in the moving image acquiring portion 110.

<1-2-1-2-3. Image Target Setting Portion 125, Area Setting Portion 140>

The image target setting portion 125 acquires m second images G2 (see FIG. 6) from the diagnosis images JG, with the period split time t being an image acquisition interval (second time interval), based on the period split time t and m second images acquired that have been set in the interval setting portion 130.

The image target setting portion 125 sets image acquisition intervals such that the time k-times the image acquisition interval (=period split time t) coincides with the predetermined part period T, thereby acquiring the first image G1 and m second images G2 from which at least a change in the predetermined part period T is recognizable (see FIG. 6). This enables appropriate medical diagnosis for a change in the predetermined part period T.

When the relationship m=k holds (see FIG. 6), the image target setting portion 125 acquires the subtraction images corresponding to a time variation in one first predetermined part period T as the first image G1 and m second images G2. This enables medical diagnosis customized to a time variation in the predetermined part period T.

To be specific, in the example of FIG. 6 for the times of the first image G1 and m second images G2, the image target setting portion 125 takes the diagnosis image JG (subtraction image) at the time=t0 as a first image G1, the diagnosis image JG (subtraction image) at the time=t0+t as a second image G21, the diagnosis image JG (subtraction image) at the time=t0+2t as a second image G22, the diagnosis image JG (subtraction image) at the time=t0+3t as a second image G23, and the diagnosis image JG (subtraction image) at the time=t0+4t as a second image G24, thereby acquiring the first image G1 and the second images G21-G24 where m=4.

In this embodiment, the determination at the time=t0 is automatically set based on the predetermined part period T detected by the predetermined part period setting portion 120, specifically, the maximum inhalation time B1 is set as t0. A user may interactively set t0 with a slider bar or the like while viewing an image. Alternatively, an approximate value of t0 may be input to the image generating apparatus 3 in advance and then the image target setting portion 125 may specifically determine the value of t0 after the predetermined part period setting portion 120 sets the predetermined part period T. If no diagnosis image JG (subtraction image) is present at the time=t0, the diagnosis image JG (subtraction image) nearest to the time=t0 is adopted as the first image G1. This also holds true for the second image G2.

Figure 7:
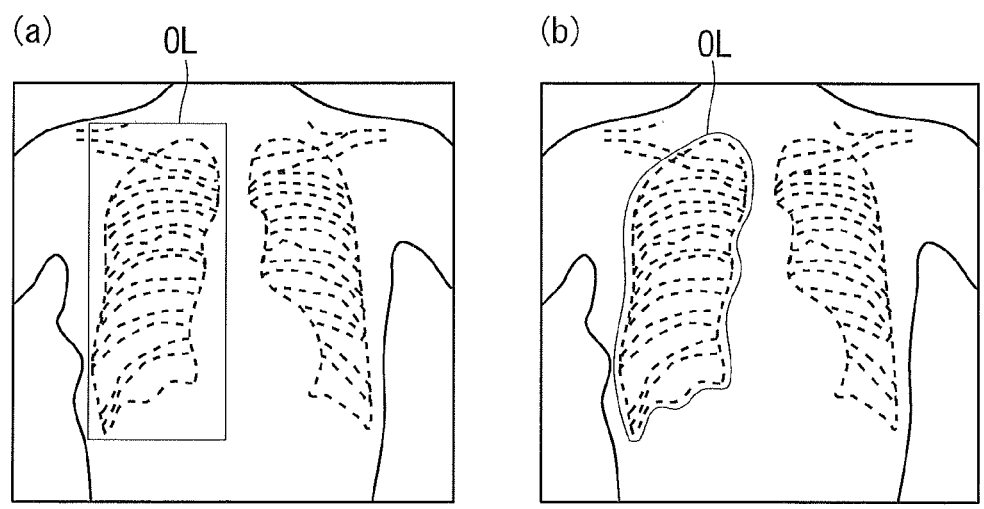
FIG. 7 is a schematic view illustrating the setting of a setting region of a diagnosis image.

The region setting portion 140 can set an attractive region in the diagnosis image JG. To be specific, the region setting portion 140 includes a contour extraction portion that extracts the contour of the lung field (predetermined part) in the diagnosis image JG, and sets a setting region based on the contour extracted by the contour extraction portion. FIG. 7 is a schematic view describing setting of a setting region in a diagnosis image JG, where part (a) of FIG. 7 shows the case in which setting is made manually and part (b) of FIG. 7 shows the case in which setting is made automatically.

In the case where the right lung field is designated as the setting region OL, in the example shown in part (a) of FIG. 7, a rectangular region is designated on an image through the operation of the operation unit 33, so that the region including the right lung field can be manually set. In the example shown in part (b) of FIG. 7, meanwhile, upon input of the instruction to designate the right lung field through the operation of the operation unit 33, the region of the right lung field is automatically detected, and the setting region OL is set so as to substantially coincide with the boundary of the right lung field. The contour extraction method involved in the respiratory information detection method, described above, is adoptable as the automatic setting technique.

The region setting portion 140 sets the setting region OL as described above, so that an image from which the state change of the portion, expected to be diagnosed, is accurately recognizable can be generated while focusing on that portion.

<1-2-1-3. Pixel Color Conversion Section 400>

Referring back to FIG. 2, the pixel color converting section 400 includes a pixel detecting portion 135, a conversion color setting portion 150, and a pixel color converting portion 145, and converts the colors of the pixels satisfying the pixel color conversion condition (predetermined condition) among pixels of the first image G1 and m second images G2 so as to be distinguishable.

The pixel color converting section 400 can also convert, based on the conversion color settings by the conversion color setting portion 150, pixel colors such that different colors appear in the temporally continuous images of the first image G1 and m second images G2. Herein, the temporally continuous images represent two images that are temporally closest among the first image G1 and m second images G2.

The pixel color converting section 400 can further convert, based on the conversion color settings by the conversion color setting portion 150, pixel colors such that the same color appears in the first image G1 and m second images G2 for every predetermined part period.

Hereinafter, the details of the processes performed by the pixel detecting portion 135, the conversion color setting portion 150, and the pixel color converting portion 145 will be specifically described in order with reference to FIG. 2.

The pixel detecting portion 135 converts the colors of the pixels present in the setting region. In other words, the pixel detecting portion 135 detects, for the pixels of each of the first image G1 and m second images G2 set by the image target setting portion 125, the pixels satisfying the predetermined condition as the pixels for color conversion from the pixels in a selected area OL set by the region setting portion 140. Here, the predetermined condition means that the first image G1 and m second images G2 are subtraction images and have an intensity value (difference value) for each pixel, and thus, the intensity value of the pixel falls within a predetermined range. The entire image may be a target in the case where the region setting portion 140 does not set the selected area OL or in the case where the region setting portion 140 itself is not provided.

The conversion color setting portion 150 sets the conversion colors based on the period split time t (image acquisition interval) and m set by the interval setting portion 130 described above, and based on the conversion color settings, the pixel color converting portion 145 converts the colors of the pixels for color conversion detected by the pixel detecting portion 135 for each of the first image G1 and m second images G2.

In this embodiment, the conversion color setting portion 150 converts the conversion colors into the colors other than black and white. To be specific, for X-ray moving images, the pixel colors have only intensity values. Thus, the RGB values are R=G=B=i, so that display is generally made in black and white. The RGB values of the pixels for color conversion are converted such that, for example, R=G=a*i (a is a factor for adjusting an intensity value) and B=0, enabling the pixel colors to be distinguishable for the X-ray image displayed in black and white.

As described above, the pixel color converting section 400 detects the pixels satisfying the predetermined condition among the pixels present in the selected area OL as the pixels for color conversion, for each of the first image G1 and m second images G2. As a result, only the pixels in the selected area OL become targets for color conversion with respect to a time variation of the predetermined part such as the lung, whereby attention is focused on a time variation customized to the selected area OL. This further improves the convenience of users and allows for the generation of images suitable for medical purposes.

<1-2-1-4. Display Image Generating Section 500>

The display image generating section 500 generates images for display using the first image G1 and m second images G2 whose pixel color have been converted by the pixel color converting section 400 described above. In this embodiment, the diagnosis image JG is a subtraction image, and thus, the acquired first image G1 and m second images G2 are also subtraction images.

Figure 8:
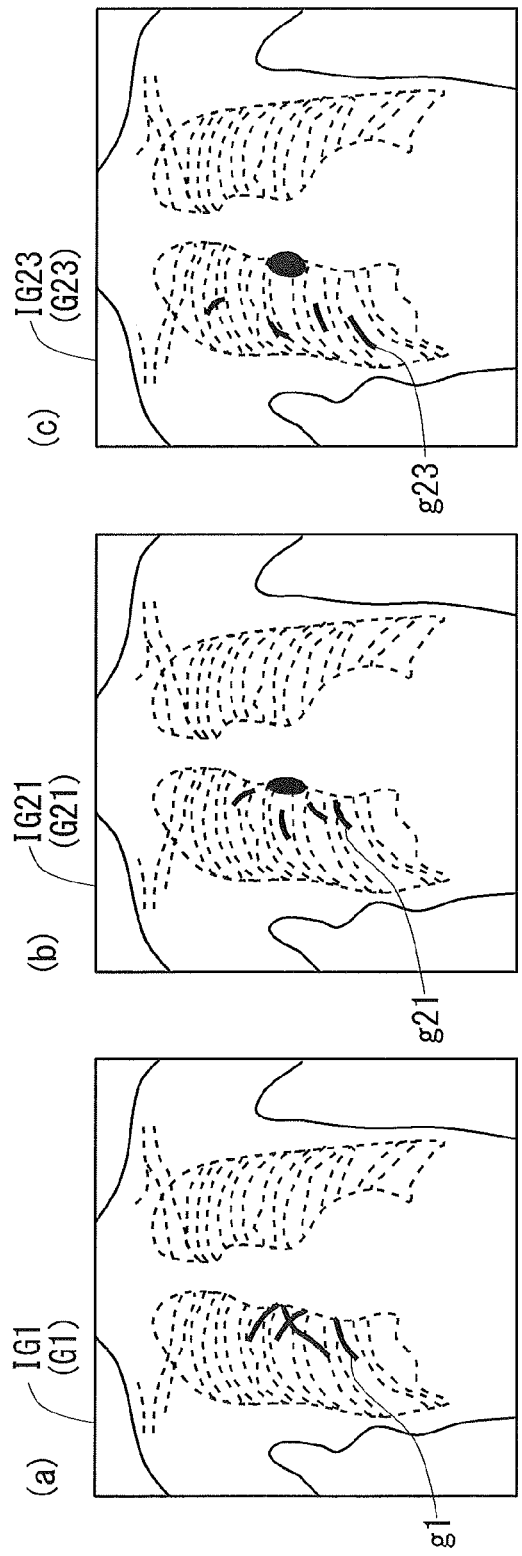
FIG. 8 is a schematic view illustrating an image for display.

FIG. 8 is a schematic view showing images for display IG1, IG21, and IG23 of the first image G1 and the second images G21 and G23 generated by the display image generating section 500 in the example of FIG. 6, where part (a) of FIG. 8 shows the image for display IG1 for the first image G1, part (b) of FIG. 8 shows the image for display IG21 for the second image G21 with m=1, and part (c) of FIG. 8 shows the image for display IG23 for the second image G23 with m=3 (see FIG. 6). A pixel (hereinafter, referred to as "first color conversion pixel") g1 that has undergone color conversion for the first image G1 and pixels (hereinafter, referred to as "second color conversion pixels") g21 and g23 that have undergone color conversion for the second images G21 and G23 preferably have different colors.

In this embodiment, the images for display IG1, IG21, and IG23 may be displayed on the display unit 34 in a temporally continuous manner, which may be repeatedly displayed.

As shown in FIG. 8, the distributions of the pixels after color conversion change in a spatio-temporal manner from a first color conversion pixel g1 (see part (a) of FIG. 8) to a second color conversion pixel g21 (see part (b) of FIG. 8) to a second color conversion pixel g23 (see part (c) of FIG. 8). In this example, the pixel color conversion condition is set and the region setting is made such that the blood flow of the right lung field region is shown. It is observed that with the lapse of time, the color conversion pixels move from the positions close to the heart to the positions apart from the heart in the right lung field region and the distribution at the position close to the heart becomes wider. Therefore, a temporal state change in the right lung field region, specifically, the state of the blood flow, can be visually recognized accurately.

The diagnosis images JG are subtraction images as described above, so that motion information can be generated readily and changing points can be clarified. The pixel colors are converted such that different colors appear in the temporally continuous images of the first image G1 and m second images G2, allowing for clear visualization of an amount of the state change of the predetermined part. This further improves the convenience of users and enables more appropriate medical diagnosis.

The pixel colors are converted such that different colors appear in the temporally continuous images among the first image G1 and m second images G2 and that the same colors appears in the first image G1 and m second images G2 for every predetermined part period T. This enables color coding in which the same color appears for every predetermined part period, whereby a periodic state change of the predetermined part can be visually recognized relatively easily.

<1-2-2. Basic Operation of Image Generating Apparatus 3>

Figure 9:
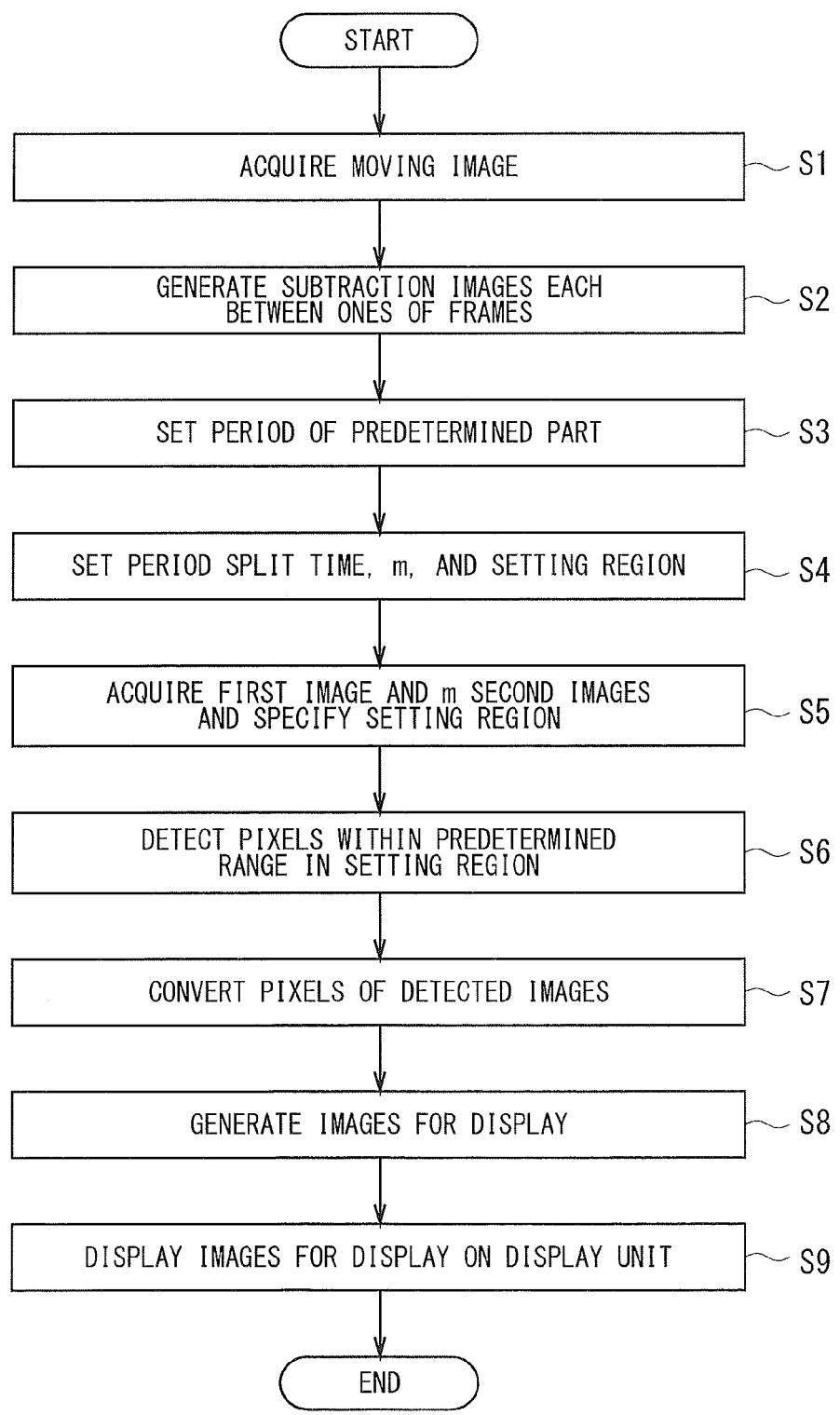
FIG. 9 is a flowchart describing the basic operation of the image generating apparatus achieved in the first embodiment.
Figure 10:
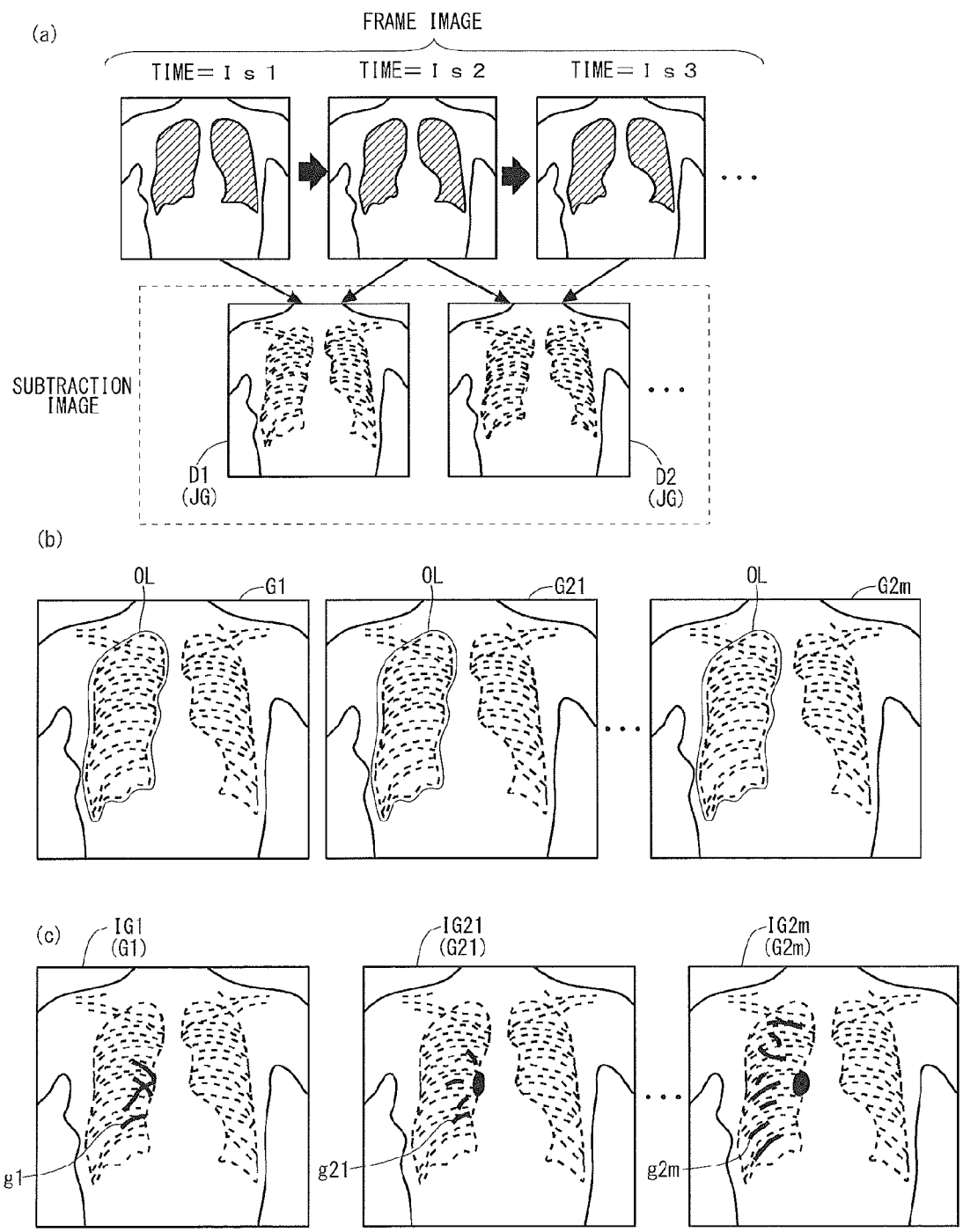
FIG. 10 is a conceptual diagram describing an overall flow in the first embodiment.

FIG. 9 is a flowchart describing the basic operation achieved in the image generating apparatus 3 according to this embodiment. FIG. 10 is a conceptual diagram showing the overall flow until images for display are generated. The individual functions of the units have been described (see FIG. 2), and accordingly, only the overall flow will be described below.

As shown in FIG. 9, first, in Step S1, the moving image acquiring portion 110 of the control unit 31 acquires a moving image photographed by the reading control device 14 of the photographing apparatus 1 through the photographing controller 2.

In Step S2, the subtraction image generating portion 115 generates, as diagnosis images JG, subtraction images each between ones of frame images in the moving image acquired in Step S1 (see part (a) of FIG. 10).

In Step S3, the predetermined part period setting portion 120 detects a periodic time variation of the geometric shape of the lung and sets a period in respiration. Specifically, in the method of detecting a periodic time variation, a periodic time variation is detected based on an image feature amount of frame images in the moving image (the above-mentioned respiratory information detection method) (see FIGS. 4, 5, and 6).

In Step S4, the interval setting portion 130 sets a period split time t, which is one k-th (k is an integer not less than two) of the predetermined part period T set in Step S3, and m satisfying m≥k (see FIG. 6), and the region setting portion 140 sets a setting region OL in the diagnosis images JG.

At this time, the conversion color setting portion 150 sets conversion colors based on the period split time t (image acquisition interval) and m set by the interval setting portion 130.

In Step S5, the image target setting portion 125 acquires a first image G1 and m second images G2 based on the period split time t, m, and setting region set in Step S4, with the period split time t as an image acquisition interval, and also specifies the setting region, or, the pixels in the setting region in each of the first image G1 and m second images G21 to G2m (see part (b) of FIG. 10).

In Step S6, the pixel detecting portion 135 detects, as pixels for color conversion, the pixels whose intensity value falls within a predetermined range from the pixels in each setting region OL of the first image G1 and m second images G21 to G2m that have been specified in Step S5.

In Step S7, the pixel color converting portion 145 converts, based on the conversion colors set in Step S4, the colors of pixels for color conversion detected in Step S6 for each of the first image G1 and m second images G21 to G2m.

In Step S8, the display image generating section 500 generates an image for display IG1 and m images for display IG21 to IG2m using the first image G1 and m second images G21 to G2m whose pixel colors have been converted in Step S7 (see part (c) of FIG. 10). The distributions of the pixels after color conversion change in a spatio-temporal manner from the first color conversion pixel g1 (see part (a) of FIG. 10) to the second color conversion pixel g21 (see part (b) of FIG. 10) to the second color conversion pixel g2m (see part (c) of FIG. 10).

Lastly, in Step S9, the display image generating section 500 outputs the image for display IG1 and m images for display IG21 to IG2m generated in Step S8 to the display unit 34, so that the image is displayed on the monitor of the display unit 34, and then, the operation flow is ended.

As described above, the image generating apparatus 3 generates temporally continuous subtraction images, which are based on a moving image in which a predetermined part of a human body or an animal is photographed, as diagnosis images JG for every first time interval. For the diagnosis image JG, a first image G1 at a predetermined time and m second images G2 for every second time interval, which is longer than the first time interval from the predetermined time, are acquired. Simultaneously, the colors of the pixels satisfying the predetermined condition among the pixels of the first image G1 and m second images G2 are converted to be distinguishable, to thereby generate an image for display IG1 and m images for display IG21 to IG2m. Thus, an amount of the state change of the predetermined part can be visually recognized accurately from the first image G1 and m second images G2. This improves the convenience of users and enables appropriate medical diagnosis.

1-3. Modification of First Embodiment

An image generating apparatus 3" of a radiation dynamic image photographing system 100" in a modification of the first embodiment of the present invention generates images from which an amount of the state change of the heart can be visually recognized accurately, in association with a periodic time variation of the heart (predetermined part) of the test subject M.

Figure 11:
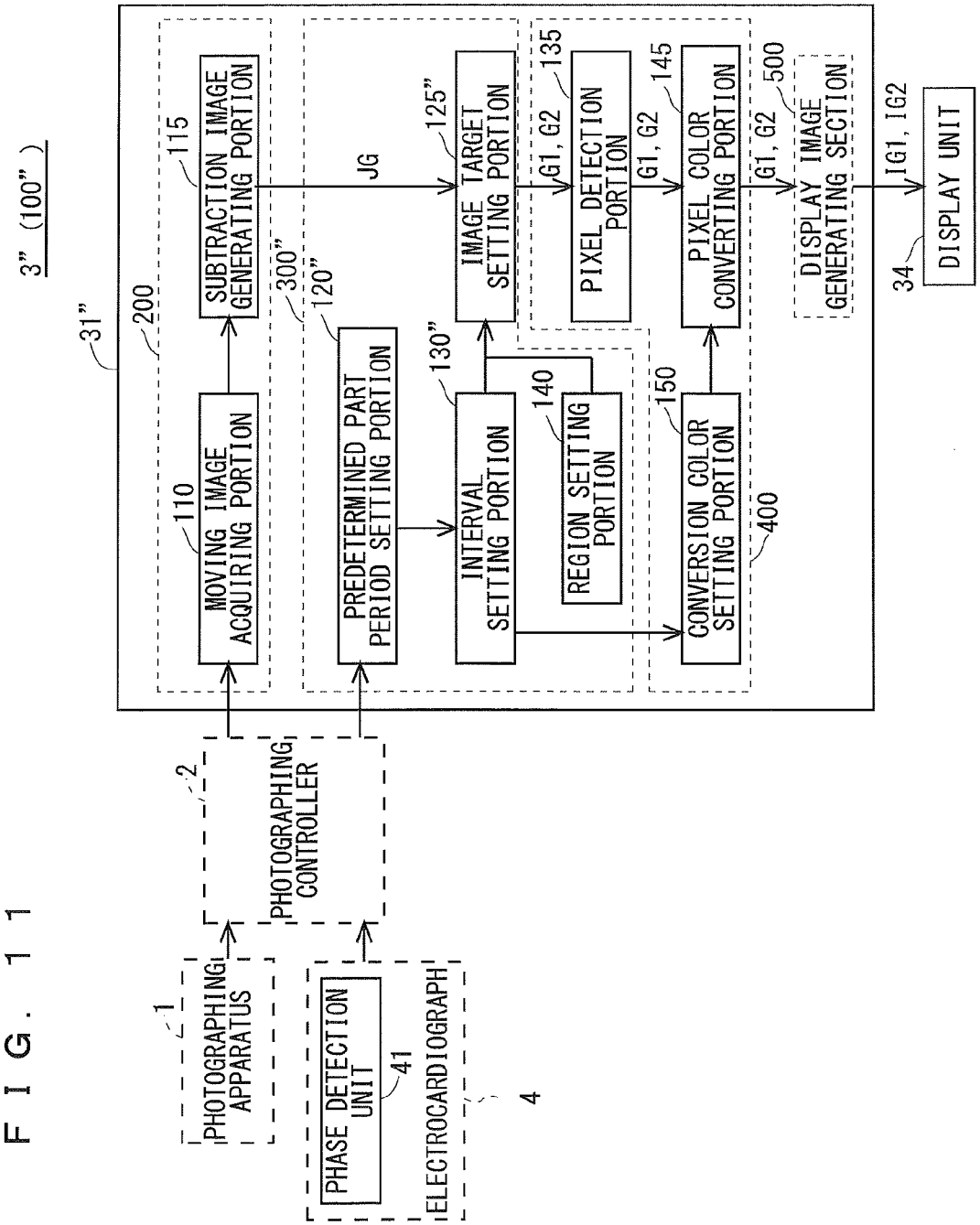
FIG. 11 is a block diagram showing the functional configuration of an image generating apparatus according to a modification of the first embodiment.

FIG. 11 shows the functional configuration of the image generating apparatus 3" in the radiation dynamic image photographing system 100".

With reference to FIG. 11, the photographing controller 2 is located between the photographing apparatus 1 and the image generating apparatus 3" (or between the electrocardiograph 4 and the image generating apparatus 3"), and the detection data stored in the storage unit 22 of the photographing controller 2 is output to the communication unit 35 of the image generating apparatus 3" through the communication unit 25.

Referring to FIG. 11, description will be given below of the functional configuration achieved by the image generating apparatus 3", which differs from that of the image generating apparatus 3 in the first embodiment.

<1-3-1. Predetermined Part Period Setting Portion 120">

The predetermined part period setting portion 120" in this modification detects a periodic time variation of the heart of the test subject M, namely, the phase information and frequency (period) information of a heart rate and sets a heart rate period (predetermined part period).

Therefore, Step S3 in the first embodiment is modified in this modification as follows. That is, the predetermined part period setting portion 120" detects a periodic time variation of the geometric shape of the heart and sets the period of a heart rate. To be specific, in the method of detecting a periodic time variation, a periodic time variation is detected based on the result acquired from the phase detection unit 41 of the electrocardiograph 4 (first heart rate information detection method) or the image feature amount of a frame image in a moving image (second heart rate information detection method), which will be described below in detail.

The method of calculating period information from heart rate will be described below.

Figure 12:
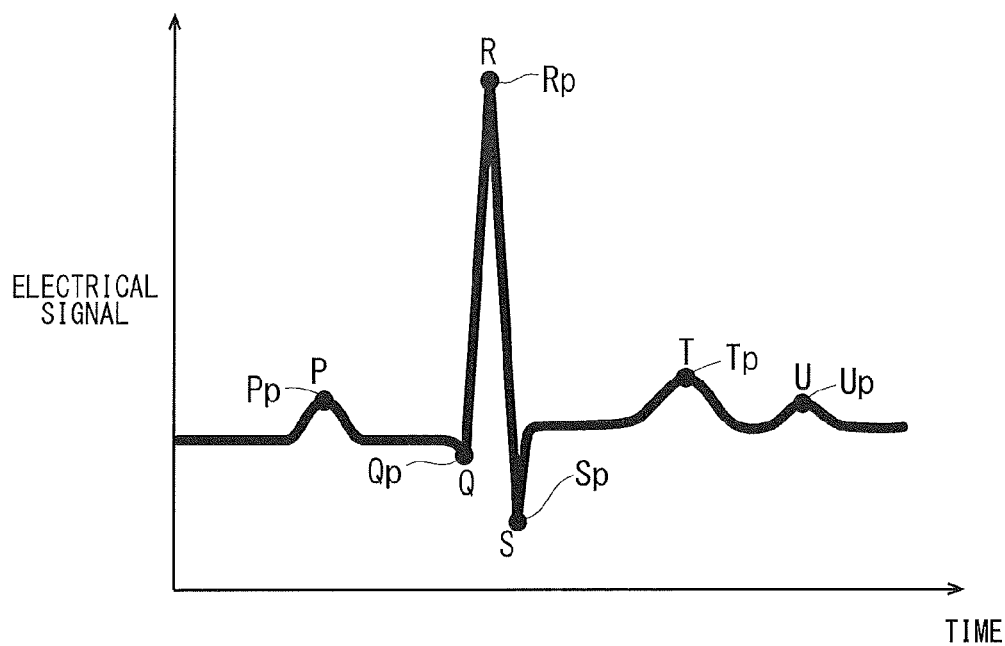
FIG. 12 is a schematic view illustrating a partial waveform measured with an electrocardiograph.

First Heart Rate Information Detection Method: Detection Result of Electrocardiograph As the first heart rate information detection method, as shown in FIG. 11, the predetermined part period setting portion 120" uses the result acquired from the phase detection unit 41 of the electrocardiograph 4. In other words, the predetermined part period setting portion 120" is configured to externally set a heart rate period. FIG. 12 illustrates one period of the electrocardiographic waveform of the test subject M. The horizontal and vertical axes of FIG. 12 represent time and the magnitude (voltage) of an electrical signal. FIG. 12 shows a curve indicating a change of an electrical signal including curves Pp, Qp, Rp, Sp, Tp, and Up representing the shapes of so-called P-wave, Q-wave, R-wave, S-wave, T-wave, and U-wave, respectively.

Therefore, the predetermined part period setting portion 120" detects the above-mentioned points (Pp, Qp, Rp, Sp, Tp, and Up) based on the detection result acquired from the phase detection unit 41, to thereby set a heart rate period.

The detection operation by the phase detection unit 41 is performed in synchronization with the photographing operation by the photographing apparatus 1 (see FIG. 1).

As described above, the predetermined part period setting portion 120" is configured to externally set a heart rate period, and thus can automatically acquire a periodic time variation of the predetermined part.

Second Heart Rate Information Detection Method: Motion Amount of Cardiac Wall

Meanwhile, as the second heart rate information detection method, as shown in FIG. 2, the predetermined part period setting portion 120" calculates the motion amount of the cardiac wall as the heart rate information using the photographed image acquired by the moving image acquiring portion 110. In other words, the moving image acquiring portion 110 of the diagnosis image generating section 200 can output a moving image to the predetermined part period setting portion 120" (see FIG. 2), and the predetermined part period setting portion 120" detects a heart rate period based on the fluctuations of the cardiac wall (changes of the shape of the predetermined part) captured in the moving image. It is premised that in addition to the lung being the predetermined part of an imaging target, the heart is captured in a moving image. More specifically, fluctuations of the cardiac wall are detected from a moving image, so that the phase of the pulsation of the heart is detected at the timing at which each frame image is photographed. The cardiac wall is accordingly detected as the phase of the pulsation of the heart.

Figure 13:
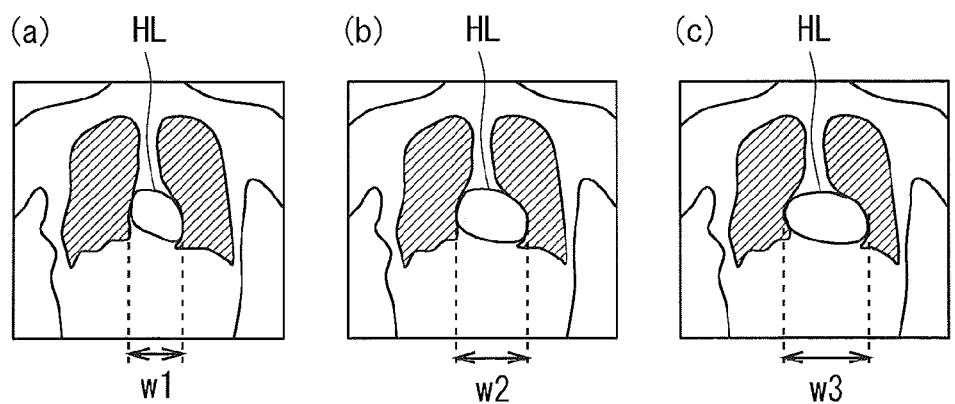
FIG. 13 is a schematic view illustrating variations of a cardiac wall.

FIG. 13 is a schematic view illustrating fluctuations of the cardiac wall captured in a moving image. As shown in FIG. 13, fluctuations in the lateral width of the heart are adopted as exemplary fluctuations of a cardiac wall HL. Parts (a) to (c) of FIG. 13 illustrate the state in which the lateral width of the heart increases from w1 to w3 during cardiac dilation.

The predetermined part period setting portion 120" detects the lateral width of the heart from each frame image, to thereby set a heart rate period. Specific examples of the technique of detecting the lateral width of the heart include the technique involving detecting the contour of the heart. Various known techniques are adoptable as the technique of detecting the contour of the heart. As an example, the following technique is adoptable: the model (heart model) showing the shape of the heart is used to align the feature point of the X-ray image and the feature point of the heart model, detecting the contour of the heart (for example, see "Image feature analysis and computer-aided diagnosis in digital radiography: Automated analysis of sizes of heart and lung in chest images", Nobuyuki Nakamori et al., Medical Physics, Volume 17, Issue 3, May, 1990, pp. 342-350).

FIG. 14 is a schematic view illustrating the relationship between the photographing time and the lateral width of the heart for a plurality of frame images constituting a moving image. In FIG. 14, the horizontal and vertical axes represent time and the lateral width of the heart, respectively, and a circle mark represents the value of the lateral width of the heart.

Here, Hwt and Hwt+1 denote the lateral width of the heart captured at a time t and the lateral width of the heart captured at a time t+1, respectively. If (Hwt+1−Hwt)≥0 holds, a frame image captured at the time t is classified as one during the cardiac dilation. If (Hwt+1−Hwt)<0 holds, a frame image captured at the time t is classified as one during the cardiac contraction.

As described above, the frame images can be classified as one during the cardiac dilation and one during the cardiac contraction by detecting fluctuations in the lateral width of the heart, namely, the cardiac wall HW, so that the phase of the pulsation of the heart can be detected.

As described above, the predetermined part period setting portion 120" detects a heart rate period based on the motion of the cardiac wall (a change in the shape of the predetermined part) captured in a moving image. This enables a heart rate period to be automatically acquired based on the motion of the cardiac wall (a change in the shape of the predetermined part) captured in a moving image.

The second heart rate information detection method indirectly detects a heart rate period compared with the first heart rate information detection method, and thus, noise components are assumed to be easily contained. Therefore, the predetermined part period setting portion 1201" preferably detects a heart rate period by frequency analysis based on the motion of the cardiac wall HL (a change in the shape of the predetermined part) captured in a moving image. Specifically, frequency analysis is performed on the fluctuations in the time-axis direction (see FIG. 14) of a partial image capturing the motion of the cardiac wall HL (region of the cardiac wall HL in FIG. 13). This enables desired fluctuation components excluding noise components to be automatically extracted, so that the motion amount of the cardiac wall HL (an amount of the state change of the predetermined part) can be grasped more accurately.

<1-3-2. Interval Setting Portion 130">

The interval setting portion 130" sets a period split time t that is one k-th (k is a positive integer) of the predetermined part period T set in the predetermined part period setting portion 120" and also sets the number m of second images satisfying m≥k.

FIG. 15 is a schematic view showing waveform data of heart rate information detected by the predetermined part period setting portion 120" in time sequence. The vertical axis corresponds to time variations of the motion of the cardiac wall. That is, FIG. 15 shows the results obtained by adopting the second heart rate information detection method to calculate a feature amount and perform monitoring in the time direction.

As shown in FIG. 15, the predetermined part period setting portion 120" sets the heart rate period T based on the point Rp (see FIG. 12), and then, the interval setting portion 130" sets the period split time t of the period T. Described here is the example in which k=3 is adopted, and the period split time t that is one third of the period T and m=6 are set. For example, if the heart rate period T is one second, the period split time t is approximately 0.34 second.

<1-3-3. Image Target Setting Unit 125">

The image target setting portion 125" acquires m second images G2 (see FIG. 15) from images for diagnosis JG assuming the period split time t is an image acquisition interval (second time interval), based on the period split time t and the number m of acquired second images set by the interval setting portion 130".

To specifically describe the case of FIG. 15 as an example, as in the description of FIG. 6, the first image G1 and second images G21 to G26 (m=6) are acquired.

2. Second Embodiment

FIG. 16 shows the functional configuration of a control unit 31A used in in an image generating apparatus 3A (see FIG. 1) configured as a second embodiment of the present invention. The control unit 31A is used as a substitute for the control unit 31 (see FIG. 2) in the image generating apparatus 3 of the first embodiment. This embodiment differs from the first embodiment in that a display image generating section 500A includes a summation image generating portion 155. The other configuration is similar to that of the image generating apparatus 3.

2-1. Summation Image Generating Portion 155

The summation image generating portion 155 generates, as an image for display IG, summation images MG of a plurality of images among the first image G1 and m second images G2 whose pixel colors have been converted.

FIGS. 17 to 19 are schematic views illustrating the results obtained by generating, as an image for display IG, a summation image MG of a plurality of images among the first image G1 and m second images G2 whose pixel colors have been converted. Here, the summation image generating portion 155 cumulatively averages the pixels values of the first image G1 and m second images G2, whose pixel colors have been converted by the pixel color converting portion 145, and calculates the resulting pixel value as the pixel value of the summation image of one diagnosis image JG (subtraction image). Then, the summation image generating portion 155 adds the distributions of a first color conversion pixel g1 and a second color conversion pixel g2 to the one diagnosis image JG in a superimposed manner, to thereby generate an image for display IG. The subjects of FIGS. 17 to 19 differ from one another.

Part (a) of FIG. 17 and part (a) of FIG. 18 illustrate, in the example of FIG. 6, the results obtained by generating the summation image MG of two images, namely, one first image G1 and one second image G21, as an image for display IG. In part (a) of FIG. 17 and part (a) of FIG. 18, the setting region is set as the right-lung-field lower region and as the right-lung-field entire region, respectively, by the region setting portion 140. In the case where the summation image MG of the two images, the first image G1 and the second image G21, is generated, as shown in part (a) of FIG. 17 and part (a) of FIG. 18, an image for display IG is generated as the summation image MG of the first color conversion pixel g1 and the second color conversion pixel g21. Here, the pixel color converting section 400 may adopt the same color for the first color conversion pixel g1 and the second color conversion pixel g21 but may convert pixel colors to differ from each other.

Part (b) of FIG. 17 and part (b) of FIG. 18 illustrate, in the example of FIG. 6 (where k=4), the results obtained by generating the summation image MG of four images (images corresponding to time variations in one respiratory period T), namely, one first image G1 and three second image G21 to G23, as an image for display IG. As in part (a) of FIG. 17 and part (a) of FIG. 18, in part (b) of FIG. 17 and part (b) of FIG. 18, the setting region is set as the right-lung-field lower region and as the right-lung-field entire region, respectively, by the region setting portion 140. In the case where the summation image MG of the four images, the first image G1 and the second images G21 to G23, is generated, as shown in part (b) of FIG. 17 and part (b) of FIG. 18, an image for display IG is generated as the summation image MG of the first color conversion pixel g1 and the second color conversion pixels g21 to g23. Here, the pixel color converting section 400 may adopt the same color for the first color conversion pixel g1 and the second color conversion pixels g21 to g23 but may convert pixel colors to differ from one another.

Parts (a) and (b) of FIG. 19 show an example in which a summation image MG of four images (images corresponding to four respiratory periods T), namely, one first image G1 and three second images G21 to G23, is generated as an image for display IG, where k=1. Part (a) of FIG. 19 shows the state in which the distributions of the first color conversion pixel g1 and the second color conversion pixels g21 to g23 agree with one another, whereas part (b) of FIG. 19 shows the state in which the distributions of the first color conversion pixel g1 and the second color conversion pixels g21 to g23 disagree with one another. In part (a) of FIG. 19, the respiration condition is stable, and thus, color conversion is performed at one sport for every period T. In part (b) of FIG. 19, meanwhile, the respiration condition is unstable, and thus, color conversion is performed at a different spot for every period T.

In the example of FIG. 19, a plurality of images for generation of a summation image MG are selected for every predetermined part period T, and pixel colors are converted to differ between temporally continuous images. This enables the periodic motion of a predetermined part to be visually recognized easily with reference to one image for display IG.

2-2. Basic Operation of Image Generating Apparatus 3A

Figure 20:
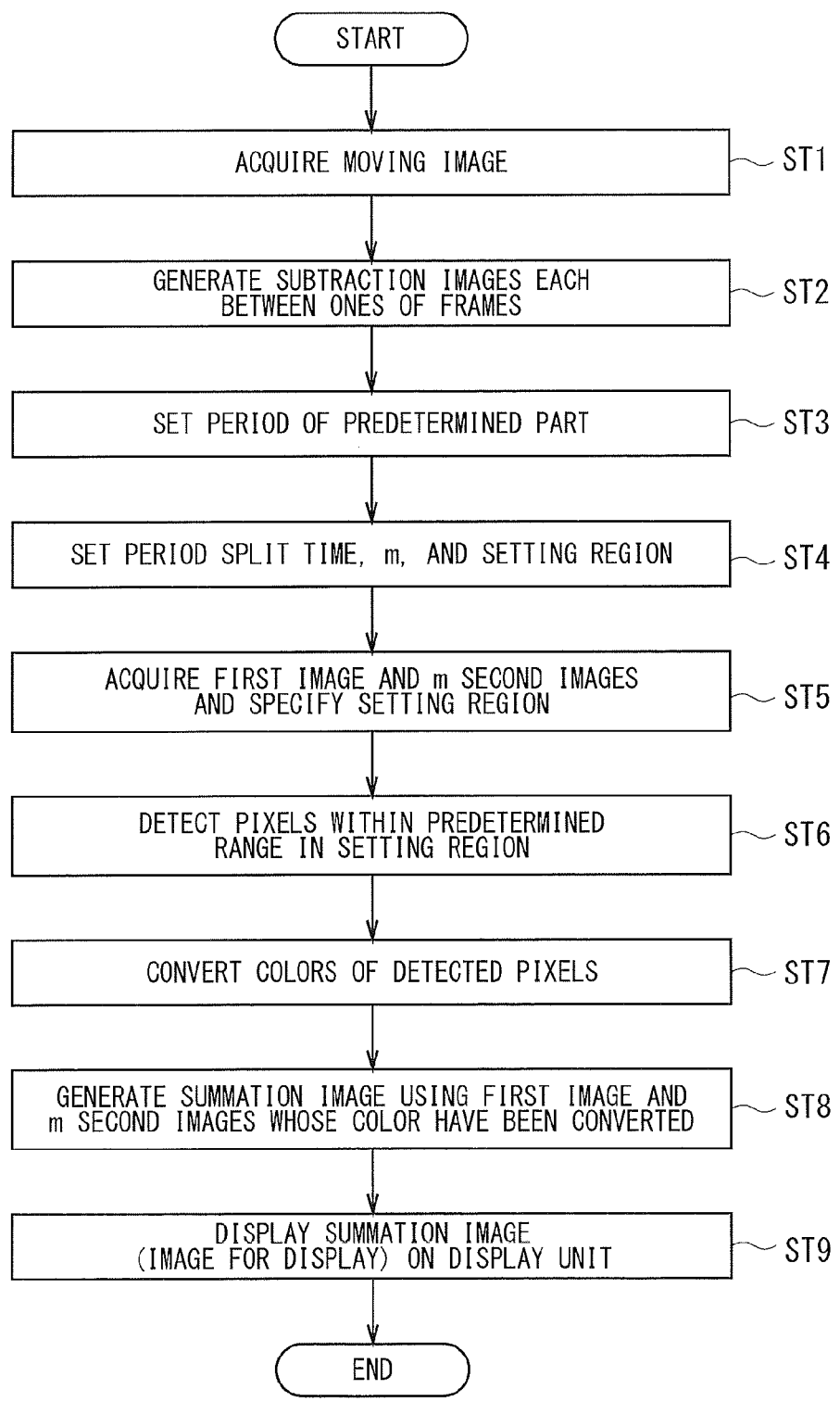
FIG. 20 is a flowchart describing the basic operation of the image generating apparatus achieved in the second embodiment.

FIG. 20 illustrates the operation flow of an image generating apparatus 3A according to the second embodiment. Steps ST1 to ST7 of FIG. 20 are similar to Steps S1 to S7 of FIG. 9, which will not be described here.

The summation image generating portion 155, which is not provided in the first embodiment, is added in the second embodiment, whereby the following steps are added in this embodiment.

After Steps ST1 to ST7 as steps similar to those of the first embodiment, as shown in FIG. 20, in Step ST8, the summation image generating portion 155 of the display image generating section 500A generates, as an image for display IG, a summation image MG of a plurality of images among the first image G1 and m second images G2 whose pixel colors have been converted in Step ST7 (see FIGS. 17 to 19).

Lastly, in Step ST9, the display image generating section 500A outputs the image for display IG generated in Step ST8 to the display unit 34, so that the image is displayed on the monitor of the display unit 34. Then, the operation flow is ended.

As described above, the image generating apparatus 3A generates, as an image for display IG, a summation image MG of a plurality of images among a first image G1 and m second images G2 whose pixel colors have converted, to thereby check the motion of a predetermined part with reference to one image for display IG.

3. Third Embodiment

FIG. 21 shows the functional configuration of a control unit 31B used in an image generating apparatus 3B (see FIG. 1) configured as a third embodiment of the present invention. The control unit 31B is used as a substitute for the control unit 31 (see FIG. 2) in the image generating apparatus 3 of the first embodiment. This embodiment differs from the first embodiment in that the diagnosis image generating section 200B includes a motion image generating portion 116 as a substitute for the subtraction image generating portion 115 of the first embodiment. The other configuration is similar to that of the image generating apparatus 3.

3-1. Motion Image Generating Portion 116

The motion image generating portion 116 generates a motion information image (vector display image) using the motion information between frame images in a moving image acquired in the moving image acquiring portion 110. In other words, a moving image (motion information moving image), from which a motion information image can be reproduced in the form of video, is generated.

A typical tracking technique such as corresponding point search processing can be used as the method of generating a motion information image. For example, in the case where the corresponding point search processing is employed, a point (corresponding point) on a corresponding-point reference image, which corresponds to an appropriate attractive point on a corresponding-point standard image, is searched for to be obtained, and motion information is obtained from the obtained relationship between the attractive point and the corresponding point, to thereby acquire a distance (motion amount, that is, an amount of the state change of a predetermined part) information from the motion information. In other words, in a moving image (time-series image) of the present invention, a previous frame image is a corresponding-point standard image and its subsequent frame image is a corresponding-point reference image. A template is set for the attractive point on the corresponding-point standard image, and a window on the corresponding-point reference image, which corresponds to the template, is searched. Then, a corresponding point is obtained from the searched window.

Figure 22:
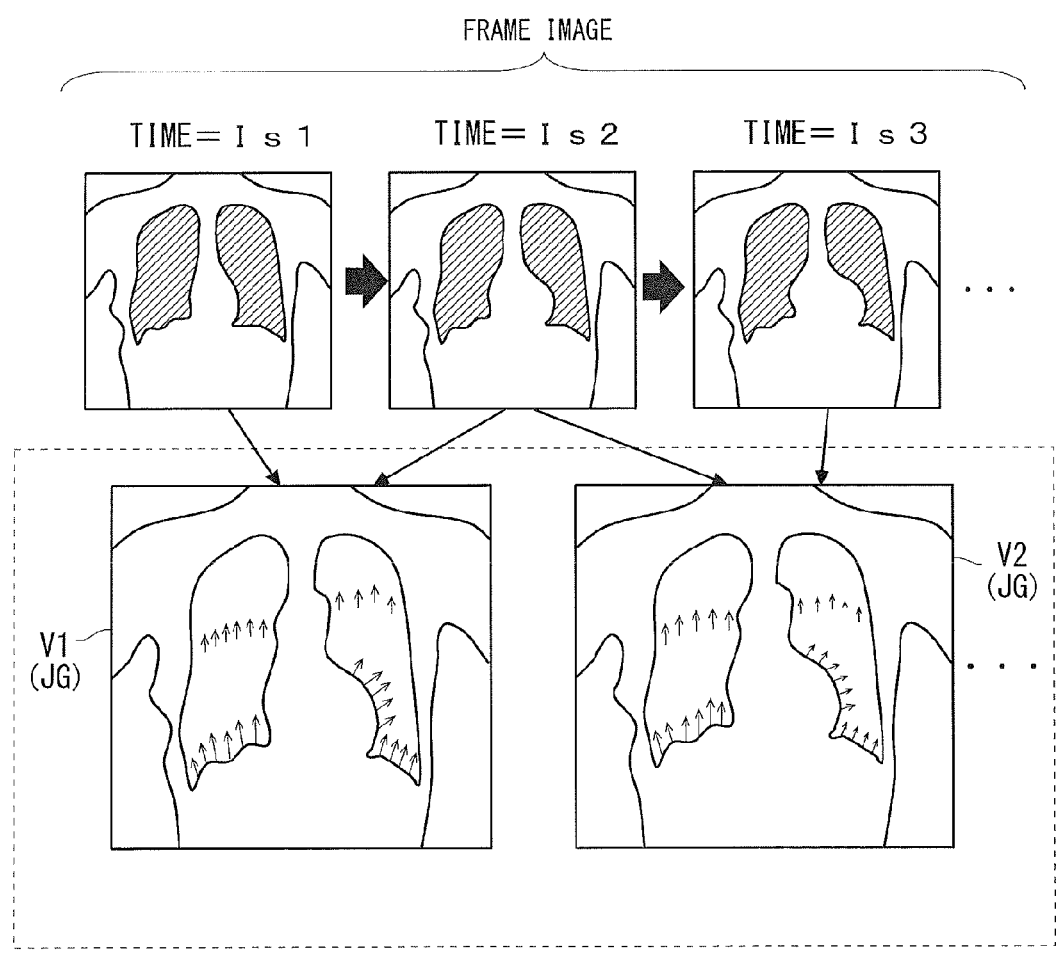
FIG. 22 is a schematic view describing the generation of a motion information image (vector display image).

FIG. 22 is a schematic view describing the generation of motion information images (vector display images) using the motion information between the frame images in the moving image acquired in the moving image acquiring portion 110. As shown in FIG. 22, for example, the above-mentioned corresponding point search processing is performed on frame images (still images) photographed individually at times Is1 to Is3. Through this processing, the motion information between the frame image (corresponding-point standard image) at the time Is1 and the frame image (corresponding-point reference image) at the time Is2 is calculated to generate a vector display image V1, where the time difference between the frame images is a motion information time difference, and the motion information between the frame image (corresponding-point standard image) at the time Is2 and the frame image (corresponding-point reference image) at the time Is3 is calculated to generate a vector display image V2, where the time difference between the frame images is a motion information time difference. Here, the motion information time difference in the present invention may be a frame interval per se of the moving image acquired by the moving image acquiring portion 110 or may be set in advance as a predetermined time interval.

Vector display images are arranged in time sequence as described above, so that a motion information moving image is generated. The generated vector display image VI (I is a finite integer) is stored in the storage unit 32 as the image for diagnosis JG.

3-2. Pixel Color Conversion Section 400B, Display Image Generation Section 500B The vector display image is employed in place of the subtraction image as the diagnosis image, and accordingly, a pixel color converting section 400B and a display image generating section 500B are changed. In particular, the pixel detecting portion 135 and the pixel color converting portion 145 of the first embodiment are modified as a pixel detecting portion 135B and a pixel color converting portion 145B in the pixel color converting section 400B in the following respects.

The pixel detecting portion 135B detects, as pixels for color conversion (that is, vectors), the pixels within a predetermined range among the pixels of a setting region, for the first image G1 and m second images G2 (vector display images). Here, the predetermined range means the range of values of the magnitude (a motion amount, namely, an amount of the state change of a predetermined part) of the vector for every pixel because the first image G1 and m second images G2 are vector display images.

The pixel color converting portion 145B converts the colors of the pixels for color conversion (that is, vectors) detected by the pixel detecting portion 135B for each of the first image G1 and m second images G2. The display image generating section 500B uses the first image G and m second images G2, whose pixel colors have been converted in the pixel color converting portion 145B, to thereby generate an image for display IG1 and m images for display IG2.

3-3. Basic Operation of Image Generating Apparatus 3

Figure 23:
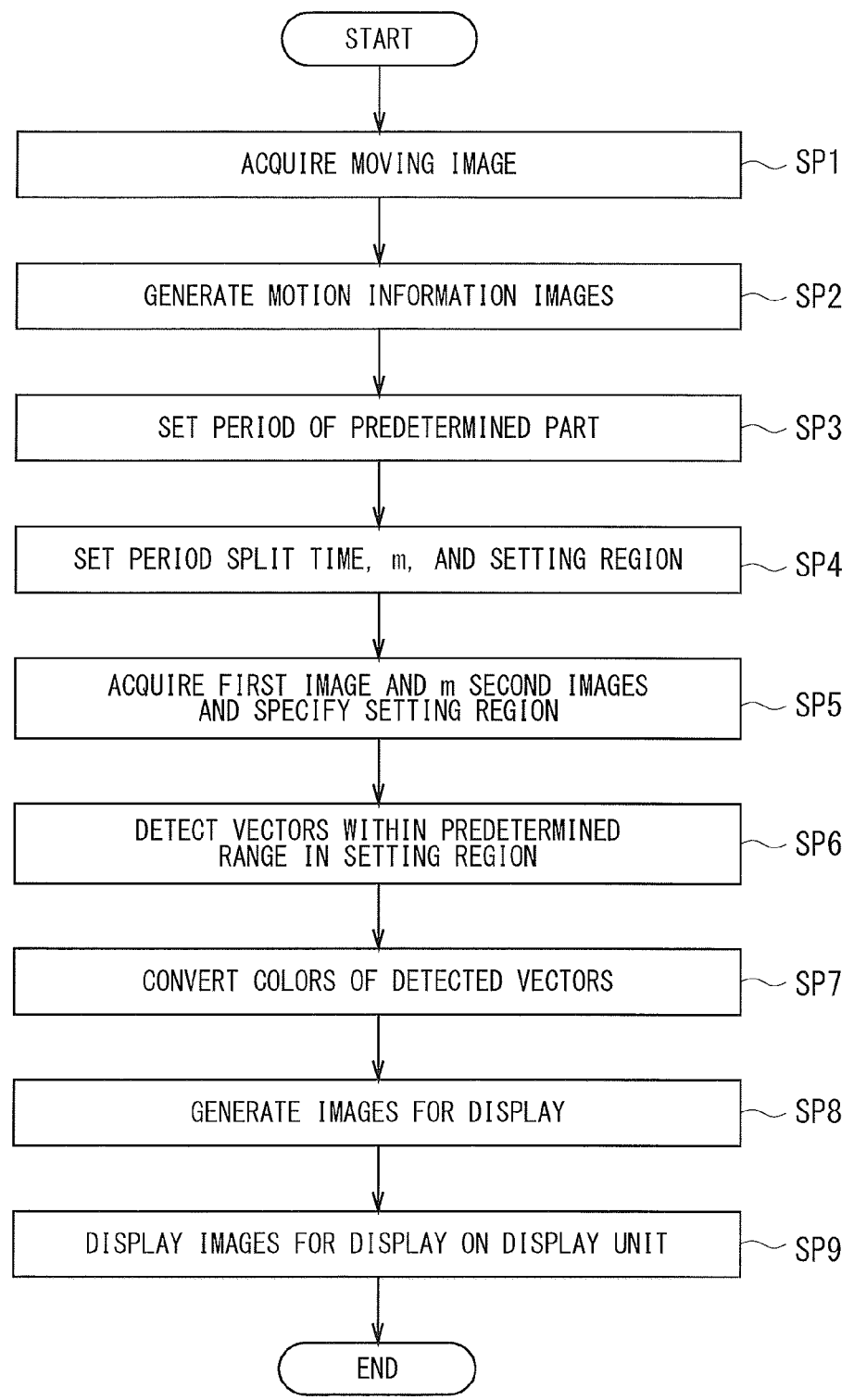
FIG. 23 is a flowchart describing the basic operation of the image generating apparatus achieved in the third embodiment.

FIG. 23 illustrates the operation flow of the image generating apparatus 3B according to the third embodiment. Steps SP1 and SP3 to SP5 of FIG. 23 are similar to Steps S1 and S3 to S5 of FIG. 16, which will not be described here.

The motion image generating portion 116 that is not provided in the first embodiment is added in the third embodiment, whereby the following steps are added.

After Step SP1 as a step similar to that of the first embodiment, as shown in FIG. 23, in Step SP2, the motion image generating portion 116 generates motion information images (vector display images) using the motion information between frame images of a moving image acquired in the moving image acquiring portion 110 (see FIG. 22).

After Steps SP3 to SP5 as steps similar to those of the first embodiment, in Step SP6, the pixel detecting portion 135B detects, as pixels for color conversion (that is, vectors), the pixels exceeding a predetermined threshold of a motion amount among the pixels in the setting region, for each of the first image G1 and m second images G2 (vector display images). In the third embodiment, thus, the pixels exceeding the predetermined threshold of the motion amount among the pixels in the setting region are the pixels satisfying the pixel conversion condition (predetermined condition).

In Step SP7, the pixel color converting portion 145B converts the colors of the pixels for color conversion (that is, vectors) detected by the pixel detecting portion 135B, for each of the first image G1 and m second images G2.

In Step SP8, the display image generating section 500B generates an image for display IG1 and m images for display IG2 using the first image G1 and m second images G2 whose pixel colors have been converted in Step SP7.

Lastly, in Step SP9, the display image generating section 500B outputs, to the display unit 34, the image for display IG1 and m images for display IG2 that have been generated in Step SP8, so that the image is displayed on the monitor of the display unit 34. Then, the operation flow is ended.

As described above, the diagnosis image is a motion information image, and thus, the image generating apparatus 3B can clarify a motion amount at a changing point (amount of the state change of a predetermined part).

4. Fourth Embodiment

Figure 24:
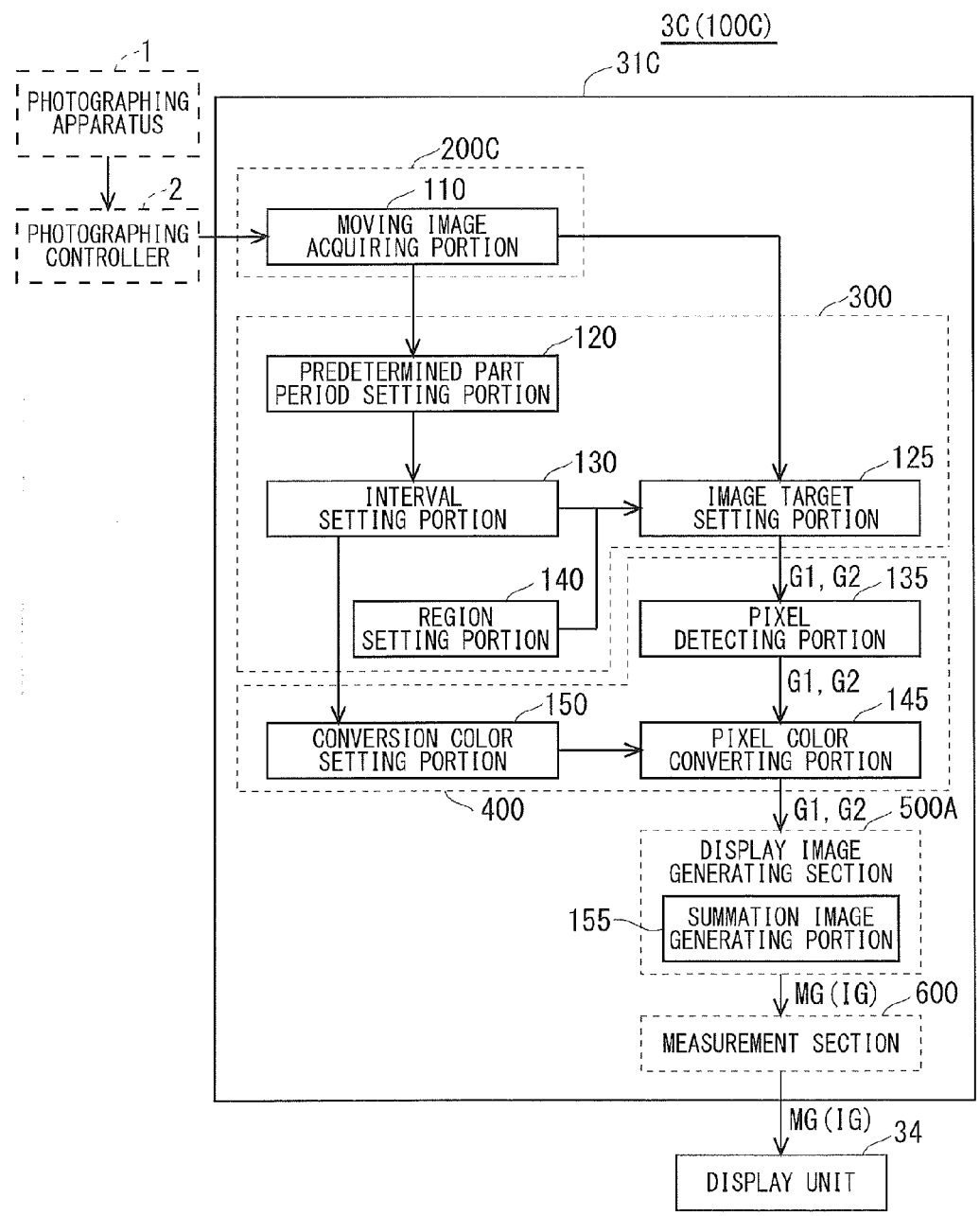
FIG. 24 is a block diagram showing the functional configuration of an image generating apparatus according to a fourth embodiment.

FIG. 24 illustrates the functional configuration of a control unit 31C used in an image generating apparatus 3C (see FIG. 1) configured as a fourth embodiment of the present invention. The control unit 31C is used as a substitute for the control unit 31A (see FIG. 16) in the image generating apparatus 3A of the second embodiment. This embodiment differs from the second embodiment in that a measurement section 600 is newly added. This embodiment takes into account the case where a diagnosis image generating section 200C includes only the moving image acquiring portion 110 (see FIG. 24) as well as the case where a diagnosis image generating section 200C includes both of the moving image acquiring portion 110 and the subtraction image generating portion 115 (see FIG. 16). The other configuration is similar to that of the image generating apparatus 3A.

4-1. Measurement Section 600

The measurement section 600 measures, based on the summation image MG generated in the summation image generating portion 155, the movement amount of a predetermined part from the distance between colors or an area in which the same color is recognized.

Figure 25:
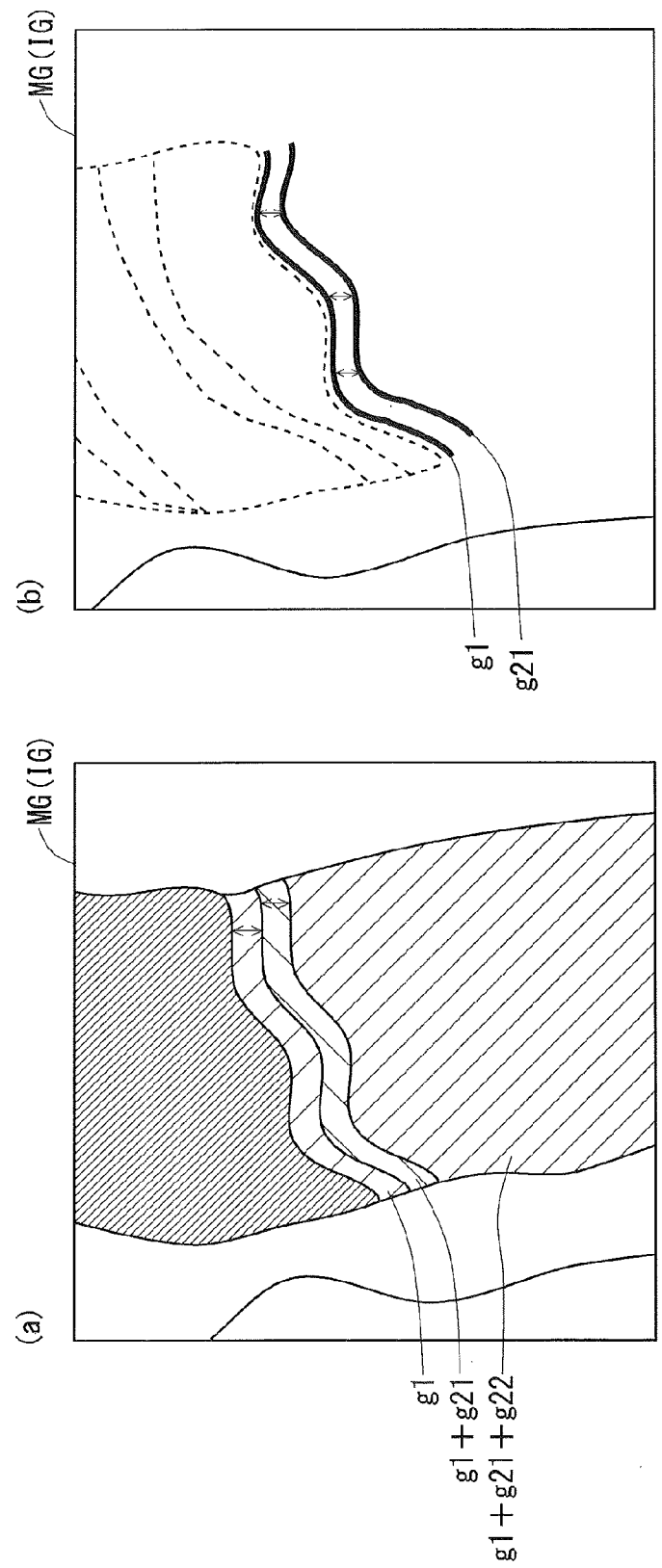
FIG. 25 is a schematic view describing the measurement of the movement amount of a predetermined part.

FIG. 25 is a schematic view describing the measurement of the movement amount of the predetermined part from an area in which the same color is recognized (see part (a) of FIG. 25) and from the distance between colors (see part (b) of FIG. 25) in the measurement section 600. Part (a) of FIG. 25 shows the case in which the diagnosis image generating section 200C includes only the moving image acquiring portion 110, where a diagnosis image is a frame image per se, and thus, a summation image MG is generated based on the frame images. Part (b) of FIG. 25 shows the case in which the diagnosis image generating section 200C includes both of the moving image acquiring portion 110 and the subtraction image generating portion 115, where a diagnosis image is a subtraction image, and thus, a summation image MG is generated based on the subtraction images.

In the example of part (a) of FIG. 25, a first color conversion pixel g1 and second color conversion pixels g21 and g22, whose colors have been converted in the respective frame images, are displayed in a superimposed manner. For example, in the case where g1 is converted into green (G), g21 is converted into red (R), and g22 is converted into blue (B), the region of only g1 is green, the region in which g1 and g21 are superimposed on each other is yellow, G+R, and the region in which g1, g21, and g22 are superimposed on one another is white, G+R+B. The measurement section 600 calculates the areas of the respective regions to measure the movement amount of the predetermined part. The region in which the color of the second color conversion pixel g22 is recognized is also included in the regions in which the colors of the first color conversion pixel g1 and the second color conversion pixel g21 are recognized.

In part (b) of FIG. 25, the first color conversion pixel g1 and the second color conversion pixel g21 are displayed in a cumulative manner, and the measurement section 600 calculates the distance between the colors of the first color conversion pixel g1 and the second color conversion pixel g22, to thereby measure the movement amount of the predetermined part.

4-2. Basic Operation of Image Generating Apparatus 3C

Figure 26:
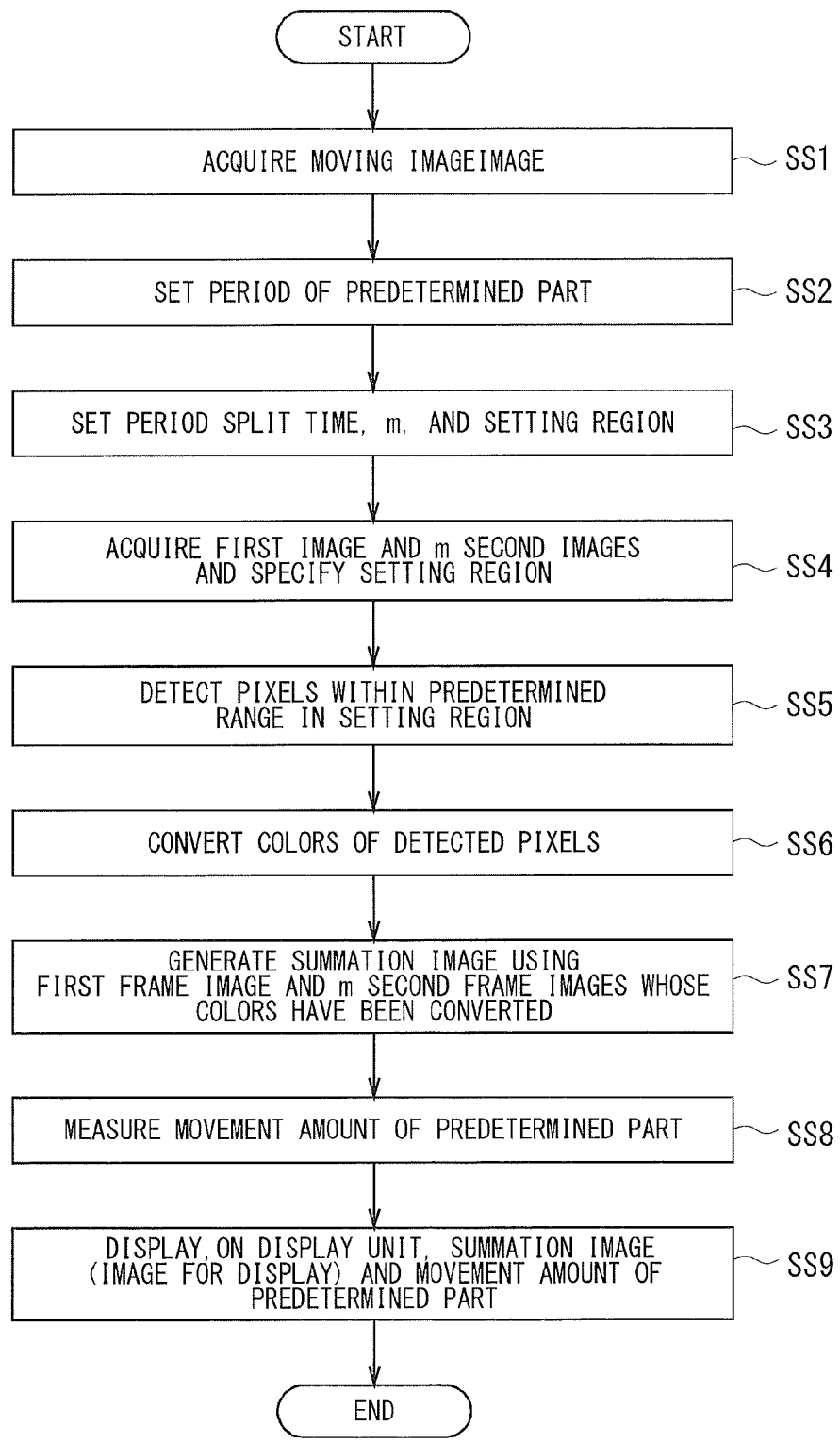
FIG. 26 is a flowchart describing the basic operation of the image generating apparatus achieved in the fourth embodiment.

FIG. 26 illustrates the operation flow of an image generating apparatus 3C according to the fourth embodiment in the case where the diagnosis image generating section 200C includes only the moving image acquiring portion 110. Steps SS1 to SS7 of FIG. 26 are similar to Steps ST1 and ST3 to ST8 of FIG. 20, which will not be described here.

The measurement section 600 that is not provided in the second embodiment is added in the fourth embodiment, and accordingly, the following steps are added.

After Steps SS1 to SS7 as steps similar to those of the second embodiment, as shown in FIG. 26, in Step SS8, the measurement section 600 measures the movement amount of the predetermined part from the distance between colors or from the area in which the same color is recognized, based on the summation image MG generated in Step SS7 (see FIG. 25).

Lastly, in Step SS9, the display image generating section 500A outputs the image for display IG generated in Step SS7 to the display unit 34, and the measurement section 600 outputs the movement amount of the predetermined part measured in Step SS8, so that the image is displayed on the display unit 34. Then, the operation flow is ended.

As described above, the image generating apparatus 3C measures the movement amount of a predetermined part from the distance between colors or from the area in which the same color is recognized, based on the summation image MG, to thereby quantify an amount of a state change of the predetermined part.

5. Modifications

While the embodiments of the present invention have been described above, the present invention is not limited to the embodiments and may be variously modified.

While the present invention has individually described the embodiments such that the image generating apparatuses 3, 3", 3A, 3B, and 3C are individually achieved, the individual functions thereof may be combined with one another unless they are inconsistent with one another.

In the present invention, a target for phase detection is the area of the portion becoming a photographing target of the body, whose geometric state changes periodically and temporally, which is not limited to the heart and lung. Alternatively, the target for phase detection may be other organs that perform involuntary movement such as peristalsis, or may be an area that performs voluntary movement, such as muscles and joints. In the latter case, kymography is performed while the same operation is repeatedly performed on a test subject.

The subject is not only the human body and may be the body of an animal.

The invention claimed is:

1. An image generating apparatus, comprising:
  a diagnosis image generating section that generates, as a diagnosis image for every first time interval, a moving image in which a predetermined part of a human body or an animal is photographed, wherein said diagnosis image generating section comprises:
    a moving image acquiring portion that acquires said moving image; and
    a subtraction image generating portion that generates a subtraction image between first frame images and second frame images in said moving image acquired in said moving image acquiring portion, wherein said subtraction image is generated by having said subtraction image generating portion subtract image data of said first frame images from image data of said second frame images, and wherein said diagnosis image is said subtraction image;
  an image target setting section that consecutively acquires a first image of said diagnosis image at a predetermined time and a second image of said diagnosis image after a second time interval from said predetermined time, wherein said second time interval is determined from said moving image and said second time interval is longer than said first time interval;
  a pixel color converting portion that converts, of pixels of said first image of said diagnosis image and said second image of said diagnosis image, colors of pixels satisfying a predetermined condition to be distinguishable; and
  a display image generating section that generates a third image for display using said first image of said diagnosis image and said second image of said diagnosis image whose colors of the pixels have been converted by said pixel color converting portion.

2. The image generating apparatus according to claim 1, wherein said image target setting section comprises a predetermined part period setting portion that sets a predetermined part period being a periodic variation of said predetermined part of said human body or said animal, and said image target setting section sets said second time interval based on said predetermined part period.

3. The image generating apparatus according to claim 1, further comprising a region setting portion that sets a setting region in said diagnosis image, wherein said pixel color converting portion converts the colors of pixels present in said setting region.

4. The image generating apparatus according to claim 1, wherein said image color conversion section comprises:
   a pixel detecting portion that detects, as pixels for color conversion, pixels having a pixel value within a predetermined range of said first image and said second images; and
   a pixel color converting portion that converts the colors of said pixels for color conversion detected by said pixel detecting portion.

5. The image generating apparatus according to claim 1, wherein said pixel color converting portion converts the colors of pixels such that different colors appear in temporally continuous images of said first image of said diagnosis image and said second image of said diagnosis image.

6. The image generating apparatus according to claim 2, wherein said pixel color converting portion converts the colors of pixels such that, of said first image of said diagnosis image and said second image of said diagnosis image, different colors appear in temporally continuous images and an identical color appears for every said predetermined part period.

7. The image generating apparatus according to claim 1, wherein said diagnosis image generating section comprises:
   a motion image generating portion that generates a motion information image using motion information between frame images in said moving image acquired in said moving image acquiring portion, and said diagnosis image is said motion information image.

8. The image generating apparatus according to claim 1, wherein said display image generating section comprises a summation image generating portion that generates, as said image for display, a summation image of a plurality of images among said first image of said diagnosis image and said second image of said diagnosis image.

9. The image generating apparatus according to claim 8, further comprising a measurement section that measures, based on said summation image, a movement amount of said predetermined part of said human body or said animal from a distance between colors or from an area in which an identical color is recognized.

10. The image generating apparatus according to claim 2, wherein said predetermined part period setting portion detects said predetermined part period based on said moving image.

11. The image generating apparatus according to claim 3, wherein: said region setting portion comprises a contour extraction portion that extracts a contour of said predetermined part in said diagnosis image, and said region setting portion sets said setting region based on said contour.

12. The image generating apparatus according to claim 1, wherein said diagnosis image generating section generates as a diagnosis image for every first time interval temporally continuous images based on said moving image.

13. The image generating apparatus according to claim 1, wherein said image target setting section sets said second time interval based on a distance between feature points of said predetermined part of said human body or said animal.

14. An image generating apparatus, comprising:
   a diagnosis image generating section that generates, as a diagnosis image for every first time interval, a moving image in which a predetermined part of a human body or an animal is photographed, wherein said diagnosis image generating section comprises:
      a moving image acquiring portion that acquires said moving image; and
      a subtraction image generating portion that generates a subtraction image between first frame images and second frame images in said moving image acquired in said moving image acquiring portion, wherein said subtraction image is generated by having said subtraction image generating portion subtract image data of said first frame images from image data of said second frame images, and wherein said diagnosis image is said subtraction image;
   an image target setting section that acquires a first image of said diagnosis image at a predetermined time and, for every second time interval from said predetermined time, a plurality of second images of said diagnosis image, wherein said second time interval is determined from said moving image and said second time interval is longer than said first time interval;
   a pixel color converting portion that converts, among pixels of said first image of said diagnosis image and said plurality of said second images of said diagnosis image, colors of pixels satisfying a predetermined condition to be distinguishable; and
   a display image generating section that generates an image for display using said first image of said diagnosis image and said plurality of second images of said diagnosis image whose colors of the pixels have been converted by said pixel color converting portion.

15. The image generating apparatus according to claim 14, wherein said image target setting section comprises:
   a predetermined part period setting portion that sets a predetermined part period being a periodic variation of said predetermined part of said human body or said animal; and
   an interval setting portion that sets a period split time being one k-th (k is a positive integer) of said predetermined part period and sets a value for m (m is a positive integer) representing the number of said second images, m satisfying m≥k, and
   said image target setting section acquires, based on said period split time and said value for m, said m second images at said period split time being said second time interval.

16. The image generating apparatus according to claim 15, wherein the relationship m=k holds.

17. The image generating apparatus according to claim 14, wherein said image color conversion section comprises:
   a pixel detecting portion that detects, as pixels for color conversion, pixels having a pixel value within a predetermined range of said first image of said diagnosis image and said plurality of second images of said diagnosis image; and
   a pixel color converting portion that converts colors of said pixels for color conversion detected by said pixel detecting portion.

18. The image generating apparatus according to claim 14, wherein said diagnosis image generating section comprises:
   a motion image generating portion that generates a motion information image using motion information between frame images in said moving image acquired in said moving image acquiring portion, and said diagnosis image is said motion information image.

19. The image generating apparatus according to claim 14, wherein said diagnosis image generating section generates as a diagnosis image for every first time interval temporally continuous images based on said moving image.

20. The image generating apparatus according to claim 14, wherein said image target setting section sets said second time interval based on a distance between feature points of said predetermined part of said human body or said animal.

21. An image generating apparatus comprising:
a control unit; and
a non-transitory storage unit in communication with said control unit, wherein said non-transitory storage unit stores a program to be executed by said control unit, said program comprising the following processes:
as a diagnosis image for every first time interval, a moving image in which a predetermined part of a human body or an animal is photographed;
generating a subtraction image between first frame images and second frame images in said moving image, wherein said subtraction image is generated by subtracting image data of said first frame images from image data of said second frame images, and wherein said diagnosis image is said subtraction image;
consecutively acquiring a first image of said diagnosis image at a predetermined time and a second image of said diagnosis image after a second time interval from said predetermined time, wherein said second time interval is determined from said moving image and said second time interval is longer than said first time interval;
converting, of pixels of said first image of said diagnosis image and said second image of said diagnosis image, colors of pixels satisfying a predetermined condition to be distinguishable; and
a display image generating section that generates a third image for display using said first image of said diagnosis image and said second image of said diagnosis image whose colors of the pixels have been converted.

22. The image generating apparatus according to claim 21, wherein said program comprises generating as a diagnosis image for every first time interval temporally continuous images based on said moving image.

23. The image generating apparatus according to claim 21, wherein said program comprises the process of setting said second time interval based on a distance between feature points of said predetermined part of said human body or said animal.

* * * * *